United States Patent
Nenoki et al.

(10) Patent No.: US 11,929,172 B2
(45) Date of Patent: Mar. 12, 2024

(54) MEDICAL EXAMINATION SUPPORT APPARATUS, AND OPERATION METHOD AND OPERATION PROGRAM THEREOF

(71) Applicants: FUJIFILM Corporation, Tokyo (JP); FUJIFILM Medical Systems USA, Inc., Lexington, MA (US)

(72) Inventors: Yasuyo Nenoki, Tokyo (JP); Junichi Ishigaki, Tokyo (JP); Keiji Sugihara, Tokyo (JP)

(73) Assignees: FUJIFILM Corporation, Tokyo (JP); FUJIFILM Medical Systems USA, Inc., Lexington, MA (US)

( * ) Notice: Subject to any disclaimer, the term of this patent is extended or adjusted under 35 U.S.C. 154(b) by 284 days.

(21) Appl. No.: 16/878,628

(22) Filed: May 20, 2020

(65) Prior Publication Data

US 2020/0279651 A1    Sep. 3, 2020

Related U.S. Application Data

(63) Continuation of application No. PCT/JP2018/042565, filed on Nov. 16, 2018.

(30) Foreign Application Priority Data

Nov. 21, 2017   (JP) ................. 2017-223841

(51) Int. Cl.
*G16H 50/20* (2018.01)
*G16H 30/40* (2018.01)
*G16H 50/70* (2018.01)

(52) U.S. Cl.
CPC ............ *G16H 50/20* (2018.01); *G16H 30/40* (2018.01); *G16H 50/70* (2018.01)

(58) Field of Classification Search
CPC ........ G16H 10/00; G16H 10/60; G16H 15/00; G16H 30/00; G16H 30/20; G16H 30/40; G16H 80/00; G16H 50/20; G16H 50/70
(Continued)

(56) References Cited

U.S. PATENT DOCUMENTS

2004/0141639 A1   7/2004  Matsui
2008/0215525 A1   9/2008  Kakimoto et al.
(Continued)

FOREIGN PATENT DOCUMENTS

JP    2008212248    9/2008
JP    2012101088    5/2012
(Continued)

OTHER PUBLICATIONS

"Office Action of Canada Counterpart Application," dated Oct. 6, 2021, p. 1-p. 8.
(Continued)

*Primary Examiner* — Joy Chng
(74) *Attorney, Agent, or Firm* — JCIPRNET

(57) ABSTRACT

There is provided a medical examination support apparatus in which the history of diagnosis can be easily grasped at a glance, and an operation method and an operation program thereof.
A screen output control unit of a medical examination support server generates a log display screen and transmits the log display screen to a client terminal. In a collective display region in the log display screen, an APL block and a MOL block are collectively displayed in a time series in a distinguishable manner. The APL block is a display block of an automatic processing log APL which is a history of automatically performing analysis processing on examination data obtained in a medical examination performed on a patient by a diagnosis support algorithm to output a result of
(Continued)

the analysis processing as diagnosis support information for supporting diagnosis of a doctor. The MOL block is a display block of a manual operation log MOL which is a history of a manual operation of the doctor with respect to the examination data.

6 Claims, 28 Drawing Sheets

(58) Field of Classification Search
USPC .......................................................... 705/2–3
See application file for complete search history.

(56) References Cited

U.S. PATENT DOCUMENTS

| | | | |
|---|---|---|---|
| 2010/0256991 A1 | 10/2010 | Ishikawa et al. | |
| 2014/0067420 A1* | 3/2014 | Ohta | G16H 80/00 705/3 |
| 2014/0324469 A1* | 10/2014 | Reiner | G16H 50/70 705/3 |
| 2015/0012887 A1* | 1/2015 | Ash | G16H 15/00 715/835 |
| 2016/0140305 A1* | 5/2016 | Takeyama | G16Z 99/00 705/3 |
| 2016/0180022 A1* | 6/2016 | Paixao | H04L 63/1408 705/3 |
| 2017/0220748 A1 | 8/2017 | Okabe et al. | |

FOREIGN PATENT DOCUMENTS

| | | |
|---|---|---|
| JP | 2013045263 | 3/2013 |
| JP | 2017134629 | 8/2017 |

OTHER PUBLICATIONS

"International Search Report (Form PCT/ISA/210) of PCT/JP2018/042565," dated Dec. 18, 2018, with English translation thereof, pp. 1-3.

"Written Opinion of the International Searching Authority (Form PCT/ISA/237) of PCT/JP2018/042565," dated Dec. 18, 2018, with English translation thereof, pp. 1-10.

"Office Action of Japan Counterpart Application" with English translation thereof, dated Apr. 13, 2021, p. 1-p. 6.

"Office Action of Australia Counterpart Application", dated Sep. 15, 2021, p. 1-p. 3.

"Search Report of Europe Counterpart Application", dated Dec. 10, 2020, p. 1-p. 9.

"Office Action of Canada Counterpart Application", dated Aug. 19, 2022, p. 1-p. 5.

"Office Action of Canada Counterpart Application", dated May 11, 2023, p. 1-p. 5.

\* cited by examiner

FIG.13

56 — LOG DATA TABLE PATIENT ID:P001 EXAMINATION DATA: CT IMAGE

| LOG ID | REGISTRATION DATE AND TIME | ALGORITHM ID | STAFF ID | IMAGE ID | QUOTATION SOURCE AND QUOTATION DESTINATION | CONTENTS |
|---|---|---|---|---|---|---|
| APL001 | 2016.01.14 10:11 | AL050 | | CT050-5 | | LESION EXTRACTION, TYPE IDENTIFICATION, SIZE MEASUREMENT |
| MOL001 | 2016.01.14 10:12 | | SF050 | CT050-5 | | ENLARGED DISPLAY OPERATION |
| MOL002 | 2016.01.14 10:18 | | SF050 | CT050-5 | | LESION MEASUREMENT OPERATION |
| QL001 | 2016.01.14 10:30 | | SF060 | CT050-5 | MOL002, RE050 | QUOTED IN MEDICAL REPORT |

| DIAGNOSIS SUPPORT INFORMATION | DOCTOR'S ANALYSIS RESULT |
|---|---|
| LESION POSITION (X, Y), TYPE A, SIZE 10×5mm, 300mm³ | LESION POSITION(XX,YY), TYPE A, SIZE 11×6mm, 330mm³ |

| PRESENCE/ABSENCE OF DETAILED INFORMATION DISPLAY | NUMBER OF TIMES OF QUOTATION | DISPLAY STATE INFORMATION |
|---|---|---|
| NOT DISPLAYED | 0 | |
| | 1 | |

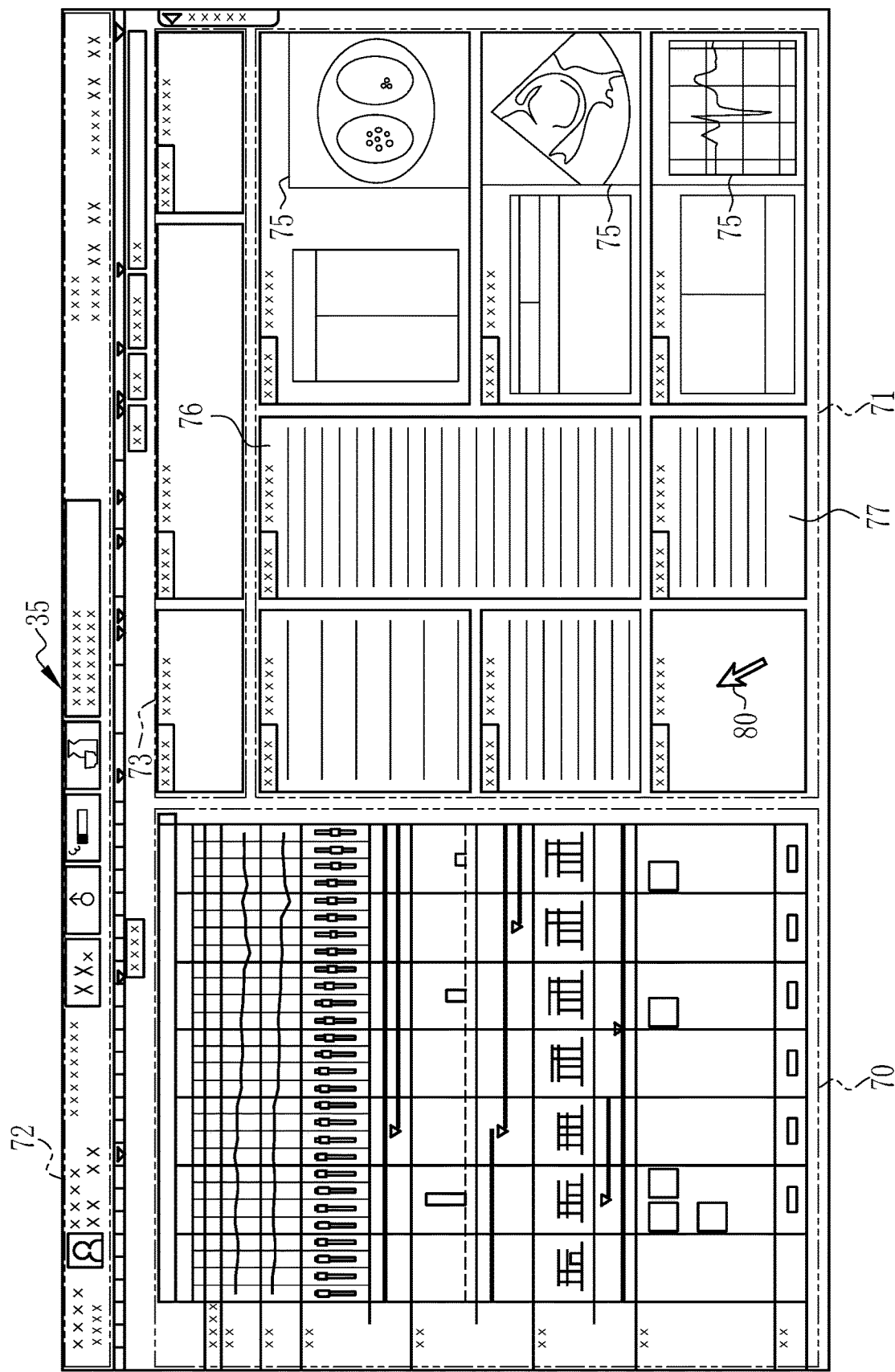

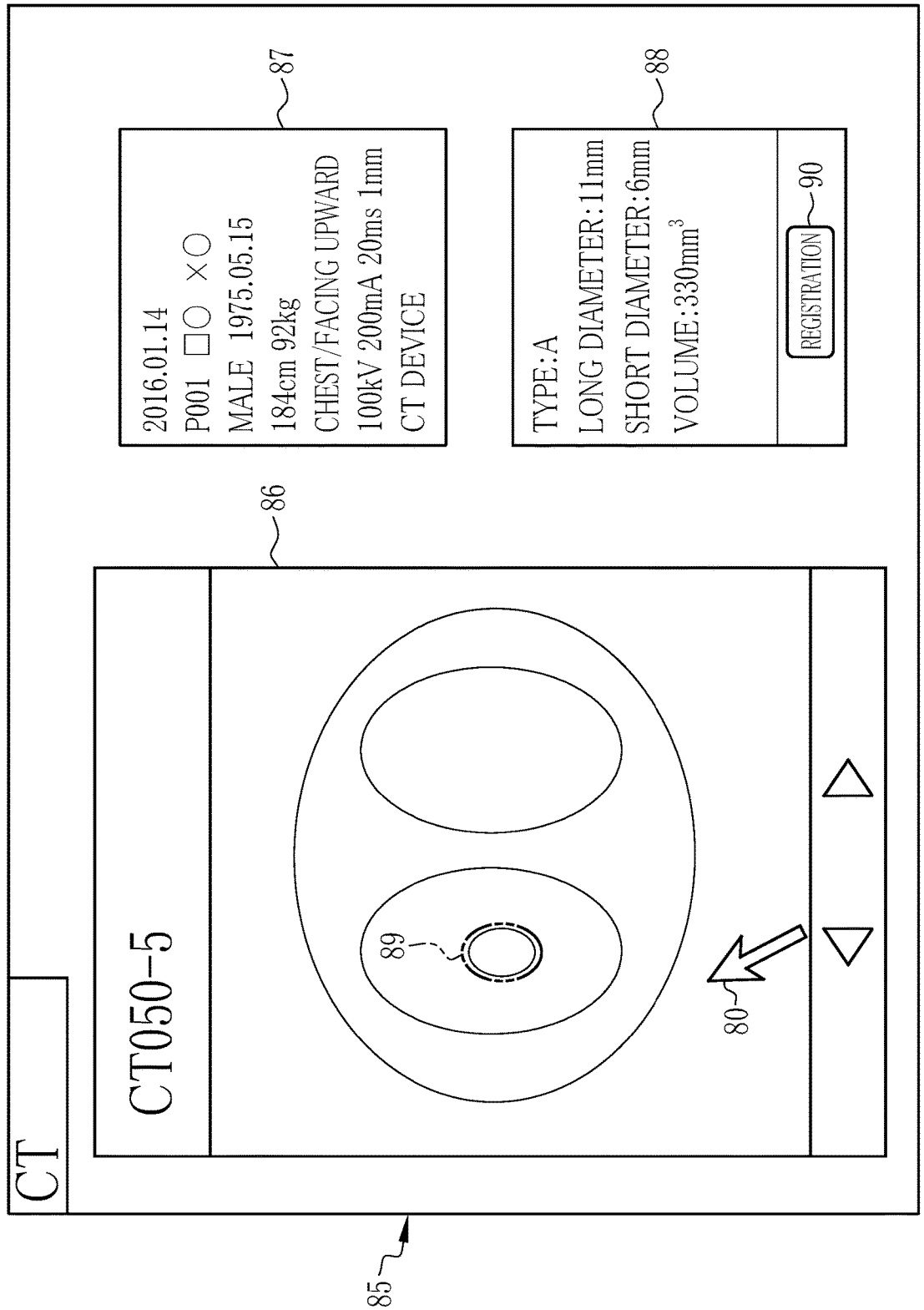

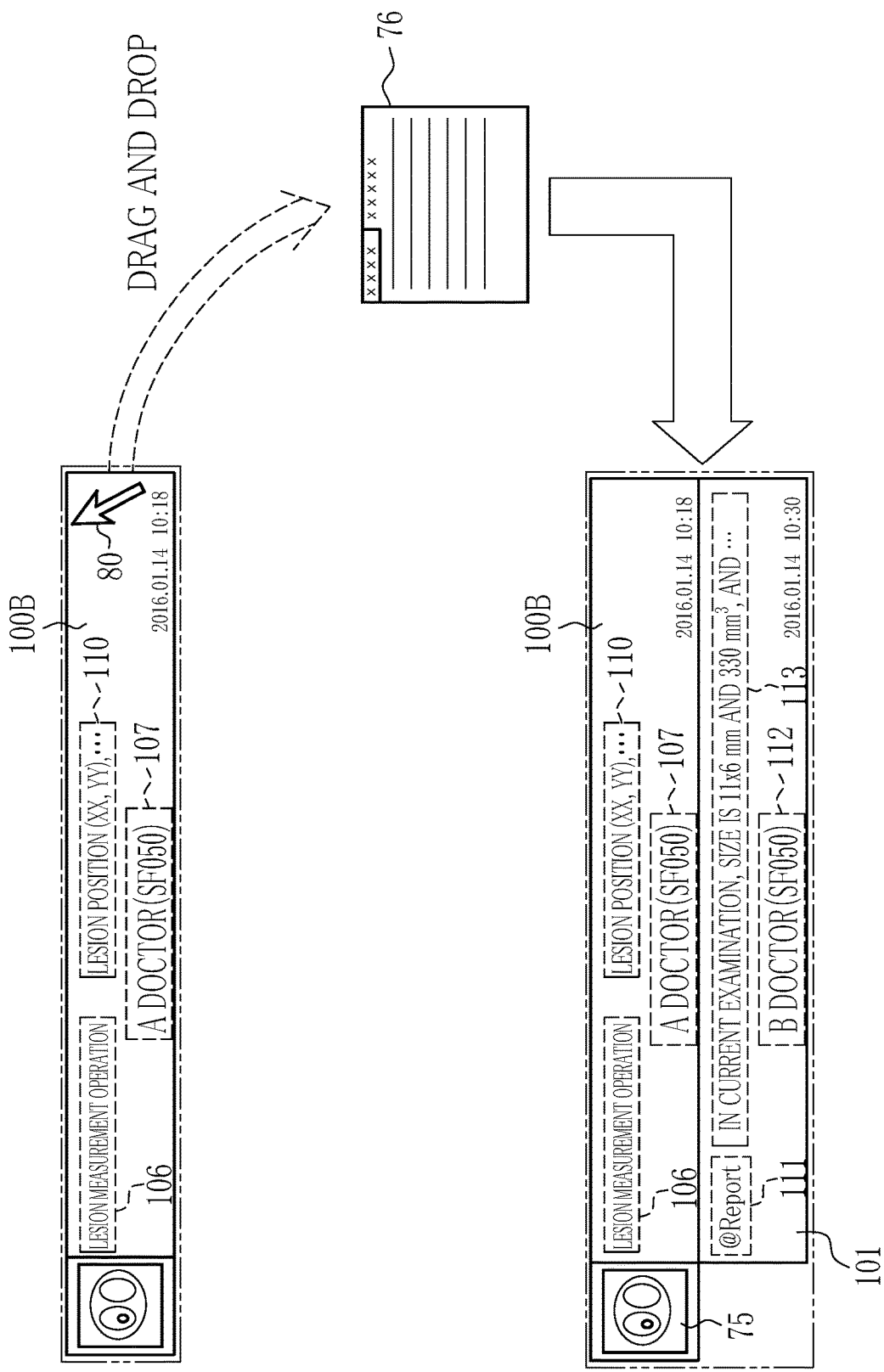

SELECTION INSTRUCTION

AFTER DETAILED INFORMATION DISPLAY

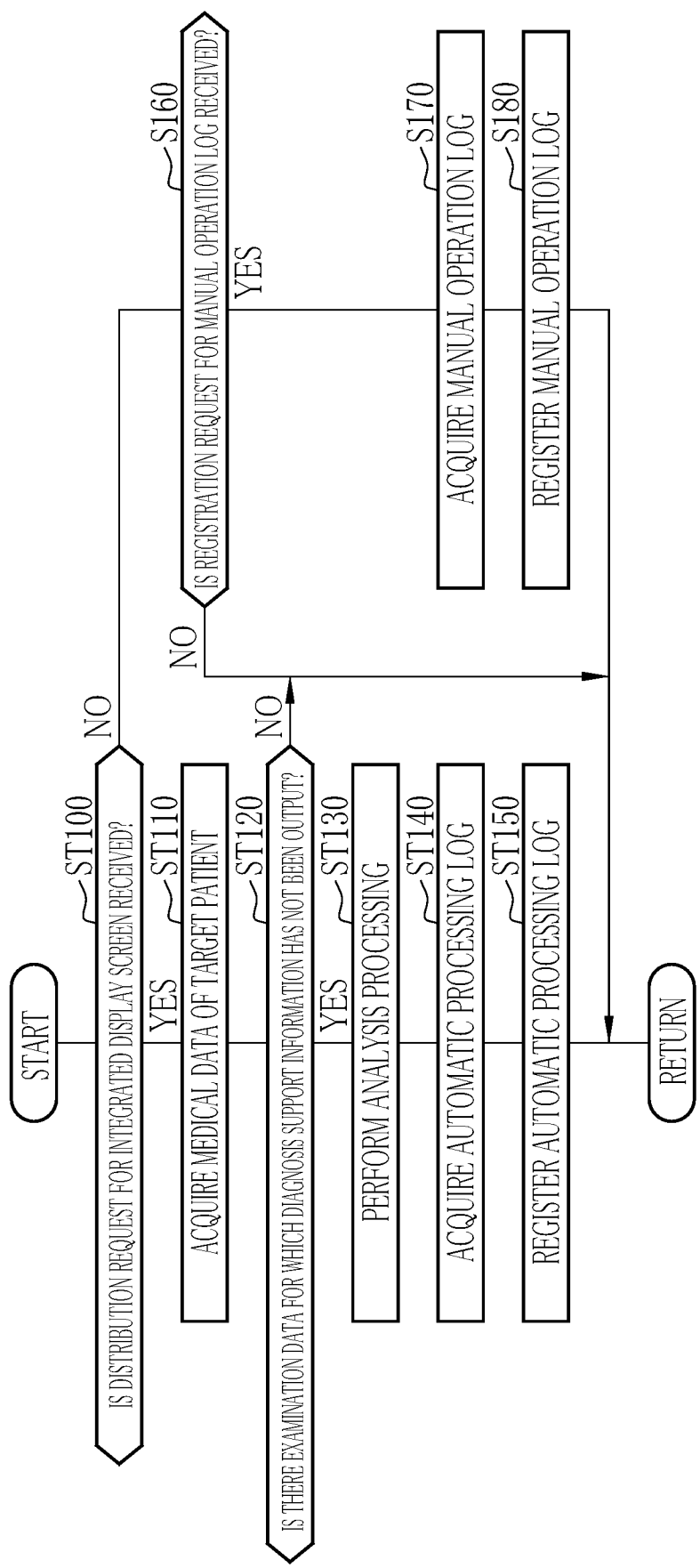

FIG.23

| NUMBER OF TIMES OF QUOTATION | DISPLAY ASPECT (BACKGROUND COLOR) |
|---|---|
| 0 | WHITE |
| 1 | YELLOW |
| 2 | YELLOW-GREEN |
| 3 OR MORE | GREEN |

MEDICAL EXAMINATION SUPPORT APPARATUS, AND OPERATION METHOD AND OPERATION PROGRAM THEREOF

CROSS-REFERENCE TO RELATED APPLICATIONS

This application is a Continuation of PCT International Application No. PCT/JP2018/042565 filed on 16 Nov. 2018, which claims priority under 35 U.S.C § 119(a) to Japanese Patent Application No. 2017-223841 filed on 21 Nov. 2017. The above application is hereby expressly incorporated by reference, in its entirety, into the present application.

BACKGROUND OF THE INVENTION

1. Field of the Invention

The present invention relates to a medical examination support apparatus, and an operation method and an operation program thereof.

2. Description of the Related Art

A doctor performs various medical examinations on a patient and views and analyzes the obtained examination data by himself/herself. For example, in a case where the medical examination is an image examination such as a computed tomography (CT) examination or a magnetic resonance imaging (MRI) examination, and the examination data is a medical image, a doctor views the medical image to extract a lesion shown in the medical image, identifies the type of the extracted lesion, and measures the size. In order to assist a doctor in performing diagnosis, recently, a diagnosis support algorithm which automatically performs analysis processing on the examination data and outputs a result of the analysis processing as diagnosis support information for supporting diagnosis of the doctor has been developed.

JP2012-101088A discloses a diagnosis support algorithm which outputs the size of a lesion in a medical image as diagnosis support information. The diagnosis support information is displayed together with the medical image. Further, in JP2012-101088A, a manual operation log (described as history of work in JP2012-101088A) which is a history of a manual operation by a doctor on the medical image, such as enlargement of the medical image by the doctor or measurement of the size of the lesion in the medical image by the doctor, is stored.

In JP2017-134629A (corresponding to US2017/0220748A1), a medical examination support apparatus which displays a manual operation log (described as history of work in JP2017-134629A), such as enlargement of the medical image by the doctor or designation of a region of a lesion in the medical image and measurement of the size of the lesion by the doctor, in time series is disclosed.

SUMMARY OF THE INVENTION

In JP2012-101088A, the diagnosis support information is displayed, and in JP2017-134629A, the manual operation log is displayed. However, in JP2012-101088A and JP2017-134629A, the relationship between an output timing of the diagnosis support information and a generation timing of the manual operation log (execution timing of the manual operation) is not particularly considered. That is, in JP2012-101088A and JP2017-134629A, it is not possible to know whether a certain manual operation is executed before the output of the diagnosis support information or is executed after the output of the diagnosis support information. Accordingly, in JP2012-101088A and JP2017-134629A, it was not possible to easily grasp what kind of thinking process the doctor proceeded with, that is, the history of diagnosis at a glance.

An object of the invention is to provide a medical examination support apparatus in which the history of diagnosis can be easily grasped at a glance, and an operation method and an operation program thereof.

In order to achieve the object, a medical examination support apparatus according to an aspect of the invention comprises a first acquisition unit that acquires an automatic processing log which is a history of automatically performing analysis processing on examination data obtained in a medical examination performed on a patient by a diagnosis support algorithm to output a result of the analysis processing as diagnosis support information for supporting diagnosis of a doctor; a second acquisition unit that acquires a manual operation log which is a history of a manual operation of the doctor with respect to the examination data; an information management unit that stores the examination data in association with the automatic processing log and the manual operation log in a storage unit; and a screen output control unit that controls an output of a log display screen which has a collective display region in which the automatic processing log and the manual operation log are collectively displayed in a time series in a distinguishable manner.

It is preferable that the manual operation log includes an analysis result for the examination data, which is input by the doctor.

It is preferable that the screen output control unit causes a quotation log to be displayed in the collective display region to correspond to the automatic processing log or the manual operation log, the quotation log being a history of quoting the diagnosis support information included in the automatic processing log or the analysis result included in the manual operation log in a medical report or a medical conference.

It is preferable that the information management unit stores the number of times of quotation of the diagnosis support information included in the automatic processing log or the analysis result included in the manual operation log, in the medical report or the medical conference in association with the automatic processing log or the manual operation log in the storage unit.

It is preferable that the screen output control unit varies a display aspect of the automatic processing log or the manual operation log depending on the number of times of quotation.

It is preferable that the medical examination is an image examination, the examination data is a medical image, and the medical examination support apparatus further includes an extraction unit that extracts the medical image of which the number of times of quotation is equal to or greater than a threshold value, as a candidate image for a similar case image similar to a medical image of a target patient.

It is preferable that the medical examination support apparatus further comprises a search unit that searches for a similar case image similar to a medical image of a target patient using an equation with the number of times of quotation as a parameter.

It is preferable a selection instruction of the automatic processing log is received in the collective display region, and the screen output control unit displays detailed information, which includes the diagnosis support information, of the automatic processing log of which the selection instruction is received, and varies a display aspect between the automatic processing log of which the selection instruction has been received and the detailed information has been displayed, and the automatic processing log of which the selection instruction has not been received and the detailed information has not been displayed.

It is preferable that a selection instruction of the manual operation log is received in the collective display region, the information management unit stores display state information representing a display state of the examination data that the doctor was viewing at a time of acquisition of the manual operation log, in association with the manual operation log in the storage unit, and the screen output control unit reproduces the display state of the examination data of the manual operation log of which the selection instruction is received, on the basis of the display state information.

An operation method of a medical examination support apparatus according to an aspect of the invention comprises a first acquisition step of acquiring an automatic processing log which is a history of automatically performing analysis processing on examination data obtained in a medical examination performed on a patient by a diagnosis support algorithm to output a result of the analysis processing as diagnosis support information for supporting diagnosis of a doctor; a second acquisition step of acquiring a manual operation log which is a history of a manual operation of the doctor with respect to the examination data; an information management step of storing the examination data in association with the automatic processing log and the manual operation log in a storage unit; and a screen output control step of controlling an output of a log display screen which has a collective display region in which the automatic processing log and the manual operation log are collectively displayed in a time series in a distinguishable manner.

An operation program of a medical examination support apparatus according to an aspect of the invention causes a computer to execute a first acquisition function of acquiring an automatic processing log which is a history of automatically performing analysis processing on examination data obtained in a medical examination performed on a patient by a diagnosis support algorithm to output a result of the analysis processing as diagnosis support information for supporting diagnosis of a doctor; a second acquisition function of acquiring a manual operation log which is a history of a manual operation of the doctor with respect to the examination data; an information management function of storing the examination data in association with the automatic processing log and the manual operation log in a storage unit; and a screen output control function of controlling an output of a log display screen which has a collective display region in which the automatic processing log and the manual operation log are collectively displayed in a time series in a distinguishable manner.

According to the invention, it is possible to provide a medical examination support apparatus which collectively displays an automatic processing log which is a history of automatically performing analysis processing on examination data obtained in a medical examination performed on a patient by a diagnosis support algorithm to output a result of the analysis processing as diagnosis support information for supporting diagnosis of a doctor, and a manual operation log which is a history of a manual operation of the doctor with respect to the examination data in a time series in a distinguishable manner, and in which the history of diagnosis can be easily grasped at a glance, and an operation method and an operation program thereof.

BRIEF DESCRIPTION OF THE DRAWINGS

FIG. 13 is a diagram illustrating more detailed contents of the log data table.

FIG. 14 is a diagram illustrating an integrated display screen.

FIG. 15 is a diagram illustrating a viewer screen.

FIG. 17 is a diagram illustrating a method of quoting diagnosis support information or a doctor's analysis result in a medical report or a medical conference.

FIG. 18 is a diagram illustrating an aspect in which detailed information of an automatic processing log of which a selection instruction is received is displayed, and a display aspect is varied between an automatic processing log of which the selection instruction has been received and the detailed information has been displayed, and an automatic processing log of which the selection instruction has not been received and the detailed information has not been displayed.

FIG. 19 is a diagram illustrating an aspect of reproducing a display state of examination data of a manual operation log of which a selection instruction is received, on the basis of display state information representing the display state of the examination data that the doctor was viewing at the time of acquisition of the manual operation log.

FIG. 20 is a flowchart illustrating a processing procedure of a medical examination support server.

FIG. 23 is a table illustrating a change example of a display aspect of an automatic processing log or a manual operation log depending on the number of times of quotation.

DESCRIPTION OF THE PREFERRED EMBODIMENTS

First Embodiment

Figure 1:
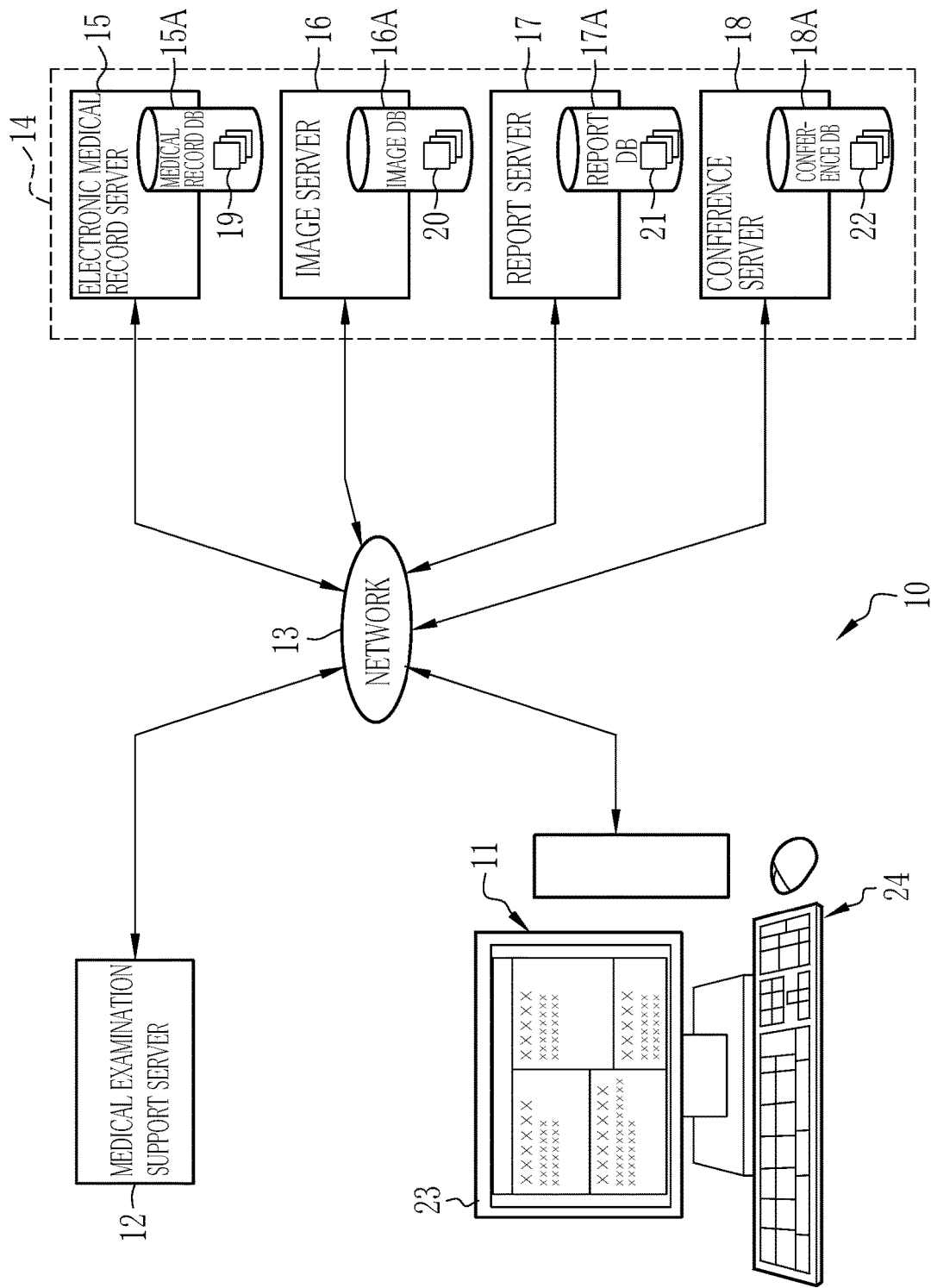
FIG. 1 is a diagram illustrating a medical examination system.

In FIG. 1, a medical examination system 10 is constructed in a medical facility, and includes a client terminal 11, a medical examination support server 12 corresponding to a medical examination support apparatus, and the like. The client terminal 11 and the medical examination support server 12 are connected to each other communicably through a network 13, such as a local area network (LAN) provided in the medical facility.

A server group 14 is also connected to the network 13. The server group 14 includes an electronic medical record server 15, an image server 16, a report server 17, and a conference server 18. The electronic medical record server 15 has a medical record database (hereinafter, referred to as DB) 15A, and electronic medical records 19 are stored in the medical record DB 15A in a searchable manner. The image server 16 has an image DB 16A, and medical images 20 obtained by various image examinations are stored in the image DB 16A in a searchable manner.

The image examination is a kind of medical examination, and the medical image 20 is a kind of examination data. The image examination includes a computed radiography (CR) examination, a CT examination, an MRI examination, an electro cardiogram (ECG) examination, a coronary angiography (CAG) examination, an ultrasonography (US) examination, an endoscopic examination, and the like. The medical image 20 of the CR examination, the CT examination, the MRI examination, or the like is created in a data file format of a digital imaging and communications in medicine (DICOM) standard, for example.

The report server 17 has a report DB 17A, and medical reports 21 in which findings resulting from the interpretation of the medical images 20 by a radiologist are summarized are stored in the report DB 17A in a searchable manner. The conference server 18 has a conference DB 18A, and conference information 22 in which contents of medical conferences are recorded is stored in the conference DB 18A in a searchable manner.

The medical conference is performed in case of deciding a future treatment plan for a patient to be treated (hereinafter, referred to as target patient) or in case of reviewing improvements in capturing of the medical image 20. The medical conference for deciding a treatment plan is performed by a plurality of medical staffs (doctors, nurses, examination technicians, and the like) in charge of treatment of the target patient while viewing the medical image 20 of the target patient. The medical conference for reviewing improvements in imaging is performed by a plurality of medical staffs (radiation technicians and the like) in charge of capturing the medical image 20 while viewing the medical image (failure image) 20 for which imaging has failed.

The client terminal 11, the medical examination support server 12, and the server group 14 are configured by installing a control program such as an operating system and various application programs based on a computer such as a personal computer, a server computer, and a workstation.

The client terminal 11 includes a display 23 for displaying various display screens, and an input device 24 such as a keyboard and a mouse, and is operated by a medical staff. In FIG. 1, only one client terminal 11 is illustrated, but a plurality of client terminals 11 are provided in practice for each medical department, such as internal medicine, surgery, examination department, and rehabilitation department, or each medical staff. The client terminal 11 is used to perform a medical examination for a patient by using various functions of the medical examination support server 12 and the server group 14.

Figure 2:
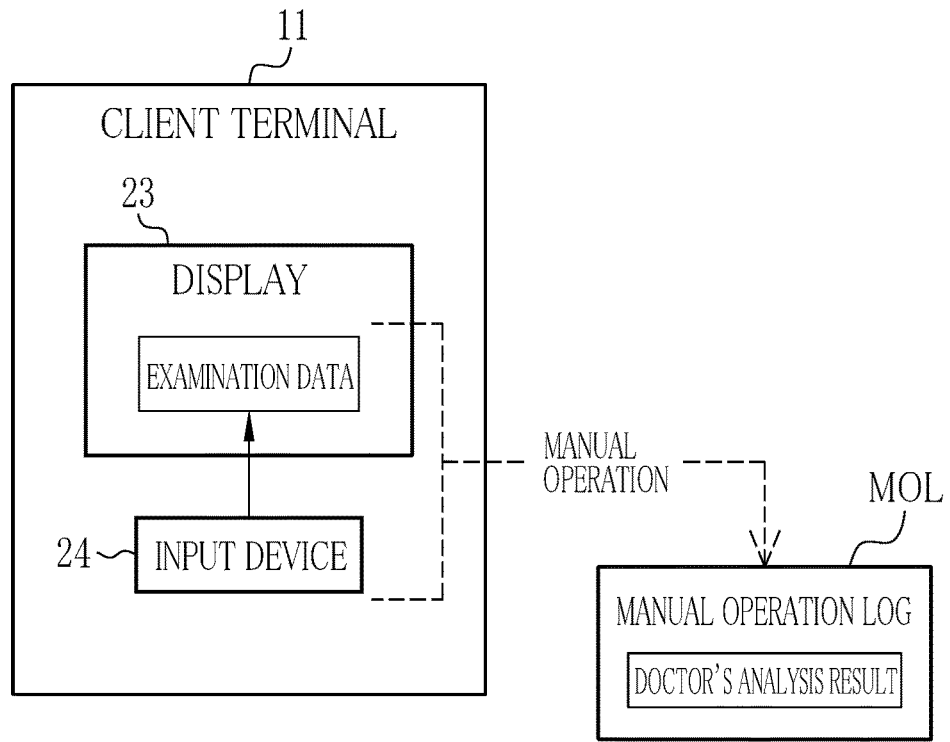
FIG. 2 is a diagram illustrating a manual operation and a manual operation log which is a history of the manual operation.

As illustrated in FIG. 2, in the client terminal 11, examination data is displayed on the display 23. The doctor can perform any input operation for the examination data displayed on the display 23 via the input device 24. The input operation of the doctor for the examination data via the input device 24 is a manual operation, and a history thereof is a manual operation log MOL. In some cases, a doctor's analysis result of the examination data is included in the manual operation log MOL.

The manual operation is, for example, enlarging the medical image 20 (enlarged display operation), instructing to display two or more medical images 20 in parallel (comparison display operation), measuring the size (long diameter, short diameter, volume, and the like) of a lesion in the medical image 20 (lesion measurement operation), inputting an annotation to the electronic medical record 19 or the medical image 20 (annotation input operation), or inputting a diagnosis name to the electronic medical record 19 (diagnosis name input operation). The doctor's analysis result is, for example, an identification result of the type of a lesion in the medical image 20, a measurement result of the size of a lesion, an annotation, a diagnosis name, or the like. Since the enlarged display operation, the comparison display operation, or the like is an operation that does not involve a doctor's analysis result, the manual operation log MOL of the enlarged display operation, the comparison display operation, or the like does not include a doctor's analysis result.

Since the medical examination support server 12 supports medical examination of the medical staff, particularly, the doctor, the medical examination support server 12 processes various kinds of medical data obtained during the medical examination for the patient and provides the results to the doctor. The medical data includes the examination data.

Figure 3:
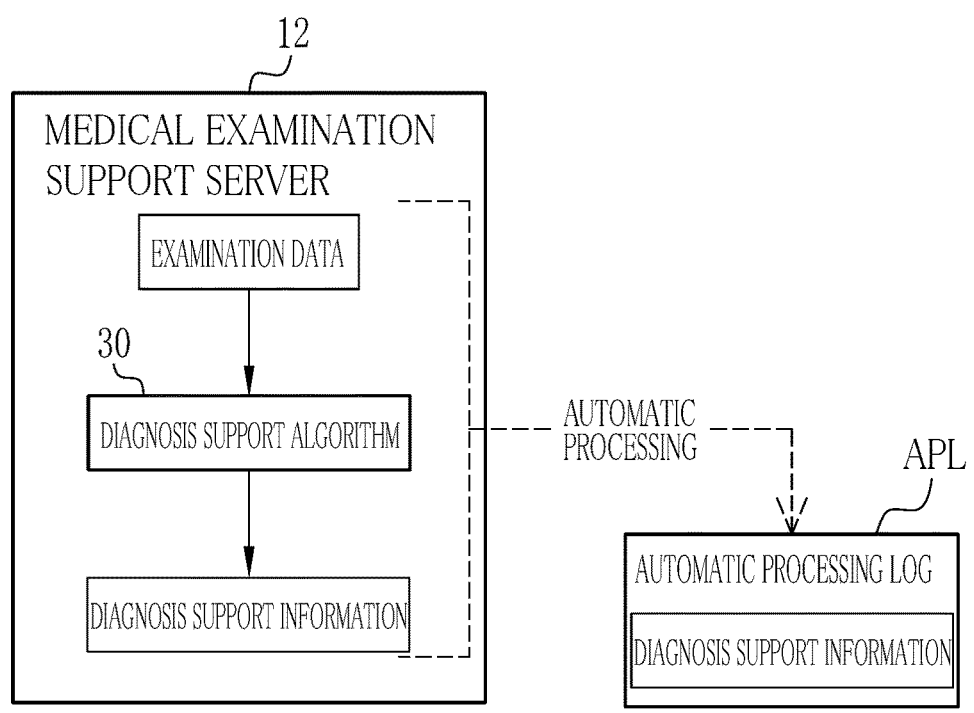
FIG. 3 is a diagram illustrating automatic processing and an automatic processing log which is a history of the automatic processing.

As illustrated in FIG. 3, the medical examination support server 12 uses a diagnosis support algorithm 30 as a part of the medical examination support. More specifically, the medical examination support server 12 inputs the examination data to the diagnosis support algorithm 30 and causes the diagnosis support algorithm 30 to automatically perform analysis processing on the examination data and output the result of the analysis processing as diagnosis support information for supporting the diagnosis of the doctor. A series of processing of causing the diagnosis support algorithm 30 to automatically output diagnosis support information is automatic processing, and a history thereof is an automatic processing log APL. The automatic processing log APL includes the diagnosis support information.

There are a plurality of diagnosis support algorithms 30. The plurality of diagnosis support algorithms 30 include, for example, one that extracts a lesion shown in a CT image, identifies the type of the extracted lesion, and measures the size of the extracted lesion. The diagnosis support information in this case is the position of the extracted lesion in the CT image, and the type and size of the extracted lesion.

Figure 4:
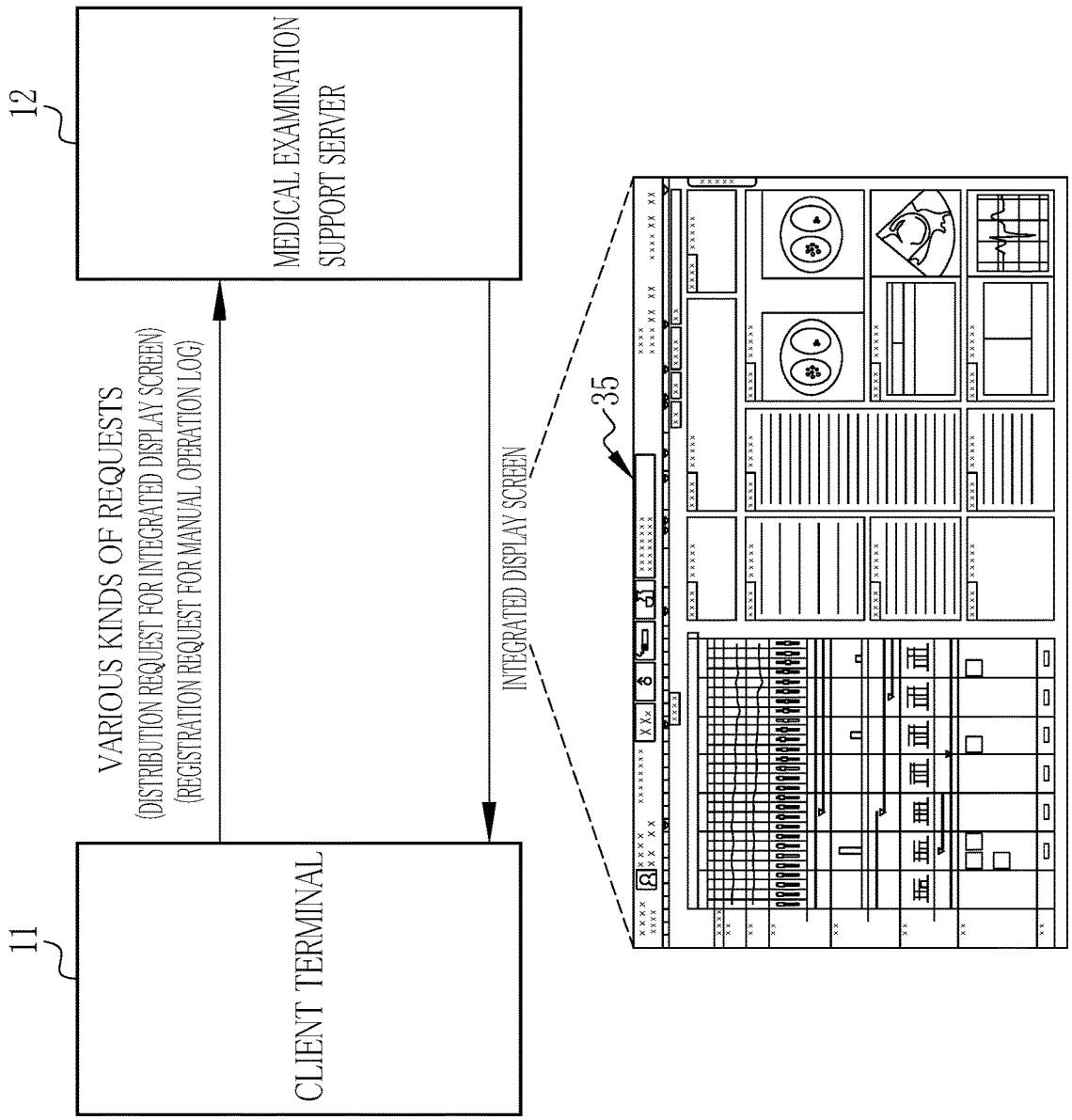
FIG. 4 is a diagram illustrating various kinds of information transmitted and received between a client terminal and a medical examination support server.

In FIG. 4, the medical examination support server 12 receives various requests from the client terminal 11. The various requests include a distribution request for an integrated display screen 35 (refer to also FIG. 14), a registration request for the manual operation log MOL illustrated in FIG. 2, and the like.

The integrated display screen 35 is a display screen in which various kinds of medical data of the target patient are combined into one for the doctor to easily perform analysis. The medical examination support server 12 acquires various kinds of medical data of the target patient according to the distribution request for the integrated display screen 35, from the server group 14, and generates the integrated display screen 35 on the basis of the acquired various kinds of medical data. The medical examination support server 12 transmits the generated integrated display screen 35 to the client terminal 11 that is a request source of the distribution request. The client terminal 11 outputs the integrated display screen 35 from the medical examination support server 12 to the display 23.

The medical examination support server 12 generates the integrated display screen 35 that can be viewed on a web browser, and transmits the integrated display screen 35 to the client terminal 11. The medical examination support server 12 issues an authentication key to the client terminal 11 to give a right for accessing the medical examination support server 12. After the client terminal 11 accesses the medical examination support server 12 and performs authentication, the integrated display screen 35 is transmitted from the medical examination support server 12 to the client terminal 11, and is displayed on the display 23.

The medical examination support server 12 outputs various display screens including the integrated display screen 35 in a format of web distribution screen data created in a markup language such as Extensible Markup Language (XML), for example. The client terminal 11 reproduces and displays various display screens on the web browser on the basis of the screen data. Instead of the XML, other data description languages, such as JavaScript (registered trademark) Object Notation (JSON), may be used.

Figure 5:
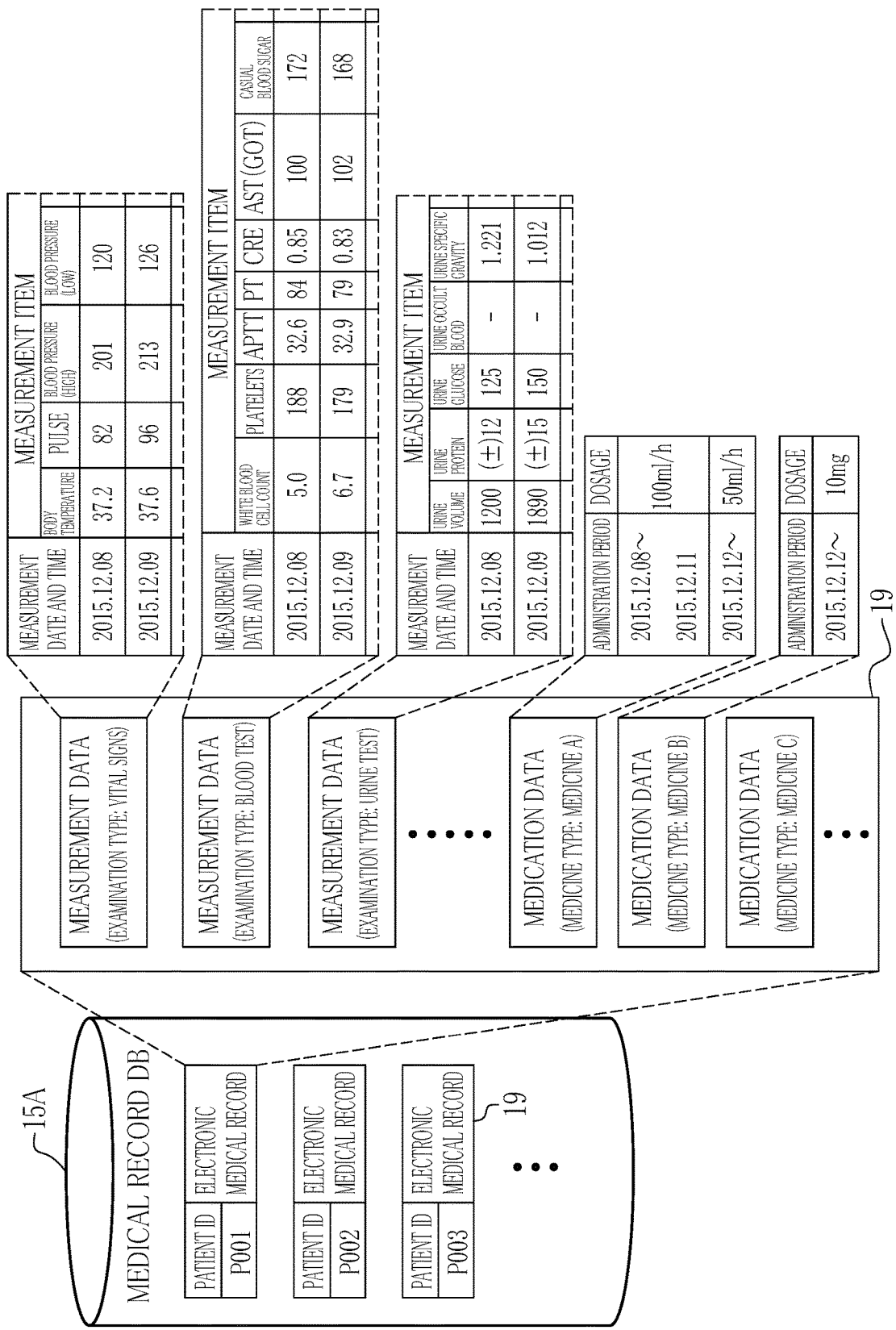
FIG. 5 is a diagram illustrating contents of electronic medical records stored in a medical record DB.

In FIG. 5, the electronic medical record 19 of the medical record DB 15A is managed for each patient in association with a patient identification data (ID) which is a symbol and a number for identifying each patient such as P001. The electronic medical record server 15 can search for the electronic medical record 19 from the medical record DB 15A using the patient ID as a search key.

The electronic medical record 19 has a plurality of pieces of measurement data and a plurality of pieces of medication data, as medical data. The measurement data is a kind of examination data as in case of the medical image 20. The measurement data is organized by type of medical examination such as vital signs, blood tests, or urine tests, and is stored in association with the measurement date and time, measurement items, and measurement values. The measurement items include, for example, in case of vital signs, the body temperature, pulse, blood pressure (high and low), and the like, and include, in case of a blood test, the white blood cell count, platelets, casual blood sugar, and the like. The medication data is organized by type of medicines such as a medicine A and a medicine B, and is stored in association with an administration period and a dosage.

In the electronic medical record 19, in addition to the patient ID, patient information such as the name, gender, age, date of birth, preference (smoking, drinking), past illness, and allergies of the patient is recorded. Further, in the electronic medical record 19, medical examination, creation of the medical report 21, orders with instructions of surgery, medication, and the like, events that occurred during the medical examination for the patient such as initial consultation, re-examination, and hospitalization, or a consultation record including patient's chief complaint and diagnosis name, a nursing record, and information from the patient's family are also recorded in time series.

Figure 6:
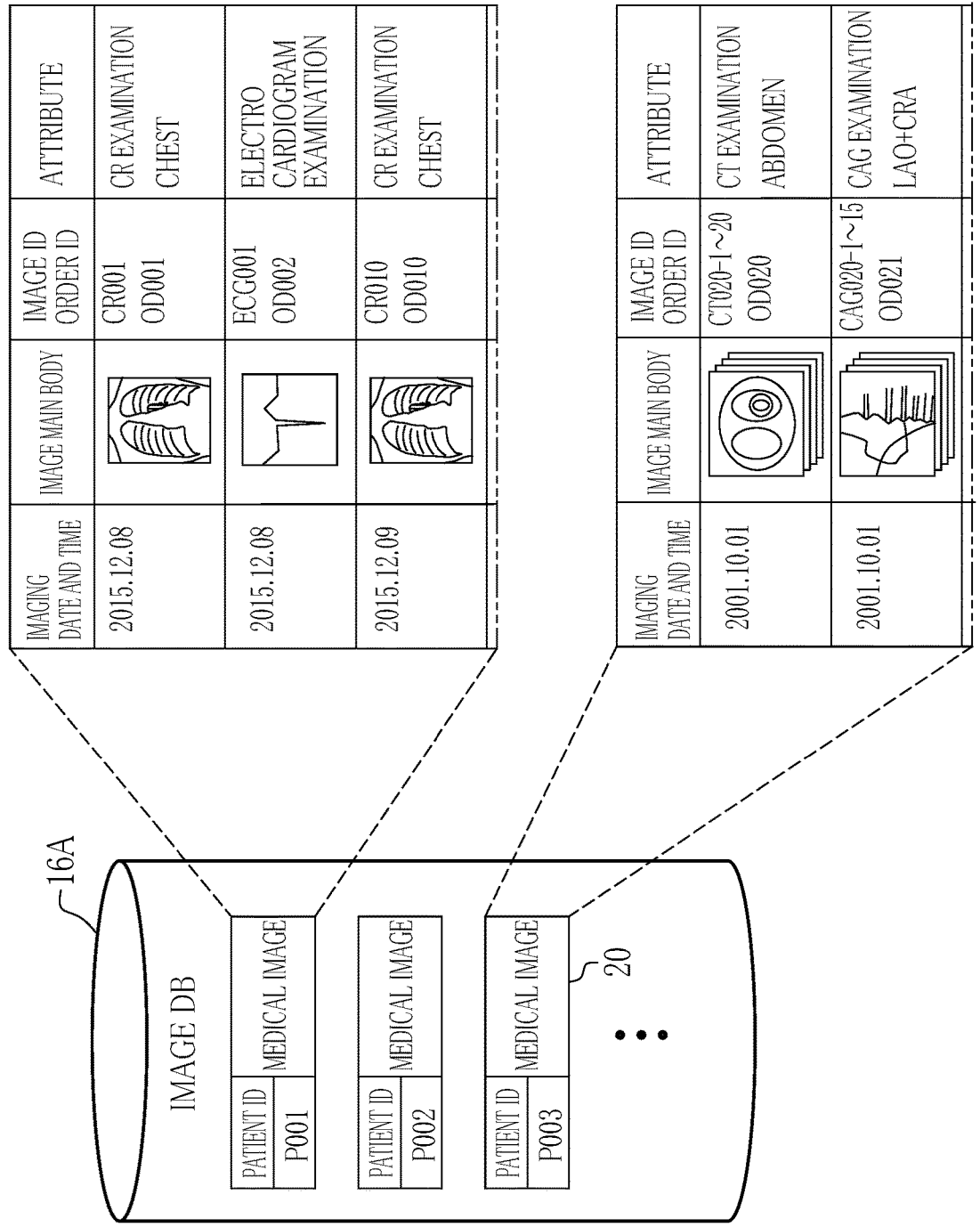
FIG. 6 is a diagram illustrating contents of medical images stored in an image DB.

In FIG. 6, the medical image 20 of the image DB 16A is managed for each patient in association with the patient ID as in case of the electronic medical record 19. As in case of the electronic medical record server 15, the image server 16 can search for the medical image 20 from the image DB 16A using the patient ID as a search key.

A file of the medical images 20 for one case includes the main body of the medical image 20, and various kinds of additional information such as imaging date and time, an image ID, an order ID, and attributes (type of image examination, imaging part, direction). The image server 16 transmits the medical image 20 together with the additional information as the medical data to the medical examination support server 12.

The image ID is a symbol and a number for identifying each medical image 20, and the order ID is a symbol and a number for identifying an order of instructing various kinds of image examinations. In case of an image examination in which a plurality of medical images 20 are captured at one time, such as CT examination or CAG examination, in order to indicate that a plurality of medical images 20 are obtained at one image examination, the medical images 20 are assigned a common order ID, and are collectively managed as the medical image 20.

Figure 7:
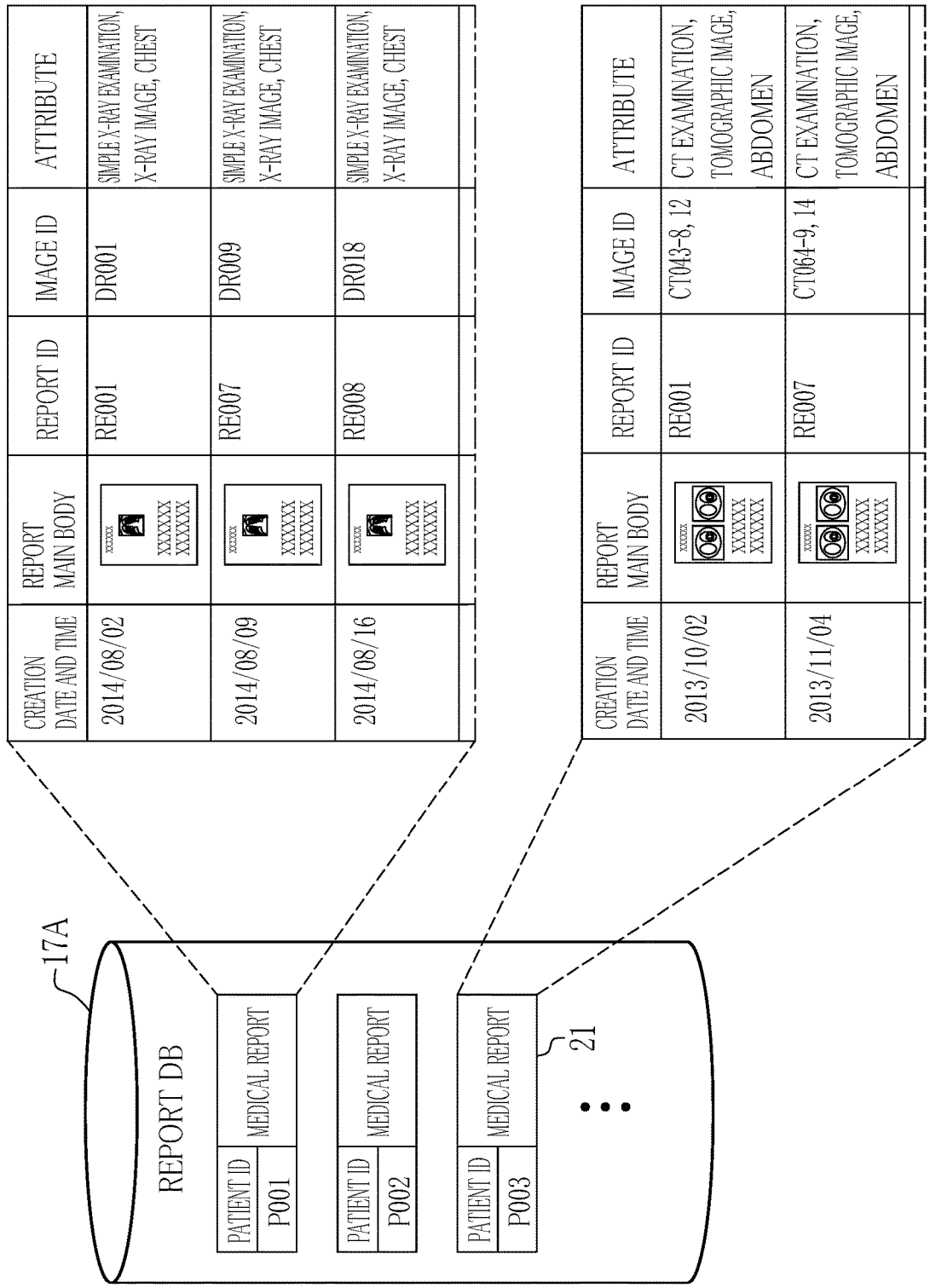
FIG. 7 is a diagram illustrating contents of medical reports stored in a report DB.

In FIG. 7, the medical report 21 of the report DB 17A is managed for each patient in association with the patient ID as in case of the electronic medical record 19 and the medical image 20. As in case of the electronic medical record server 15 and the image server 16, the report server 17 can search for the medical report 21 from the report DB 17A using the patient ID as a search key.

In the medical report 21, in addition to the patient ID, creation date and time of the medical report 21, a report ID for identifying each medical report 21, an image ID of the medical image 20 quoted in the medical report 21, and attributes similar to the medical image 20 are associated as additional information. The report server 17 transmits the medical report 21 together with the additional information as the medical data to the medical examination support server 12.

Figure 8:
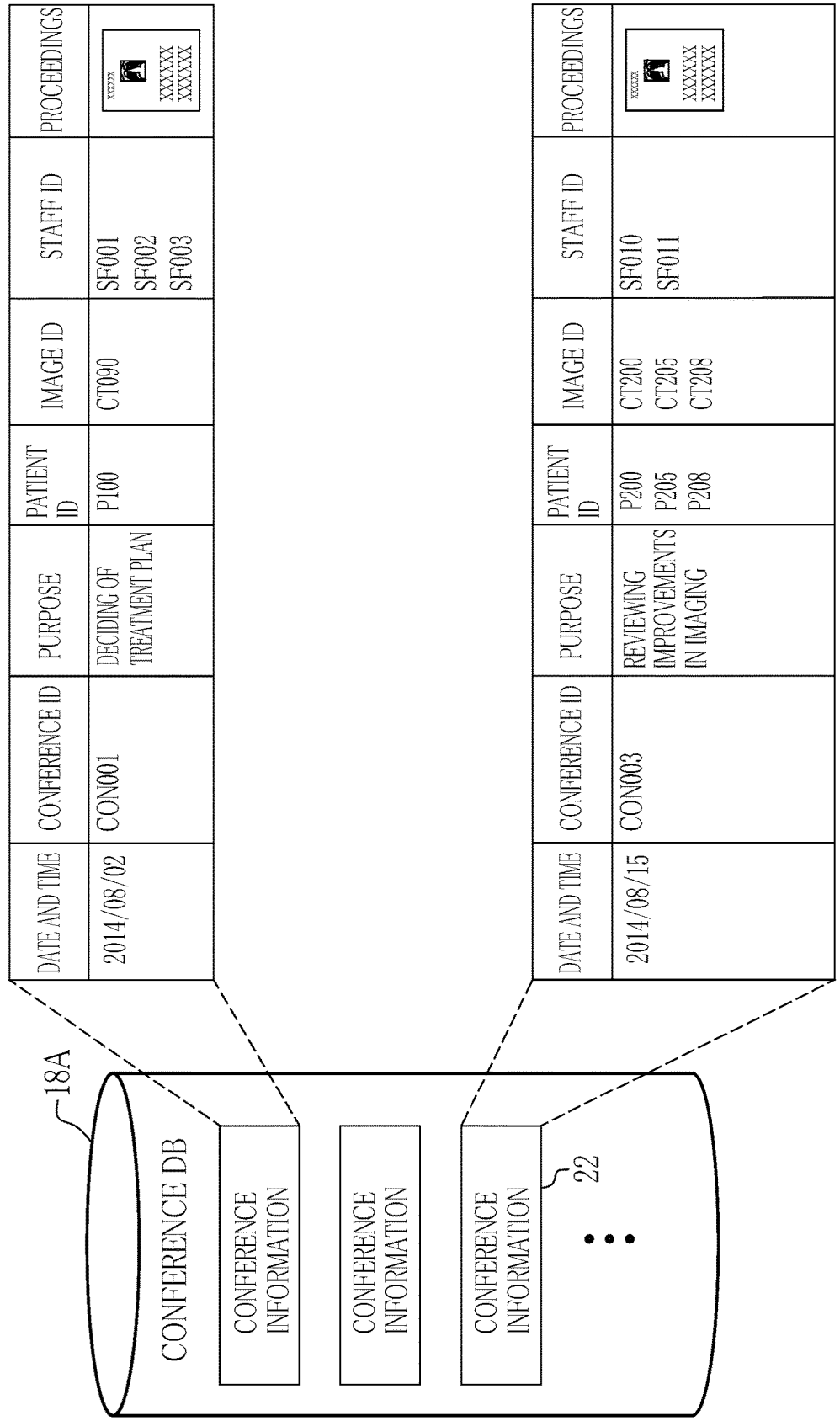
FIG. 8 is a diagram illustrating contents of conference information stored in a conference DB.

In FIG. 8, in the conference information 22 of the conference DB 18A, date and time of a medical conference, a conference ID for identifying each medical conference, a purpose of a medical conference, a patient ID of the target patient (patient of which the medical image 20 quoted in the medical conference is captured) of the medical conference, an image ID of the medical image 20 quoted in the medical conference, a staff ID for identifying a medical staff attending the medical conference, and proceedings are associated as additional information. In the proceedings, remark contents of the medical staff attending the medical conference, the summary of the medical conference, and the like are recorded. In FIGS. 5 to 8, among various kinds of date and time, only the date is illustrated.

Figure 9:
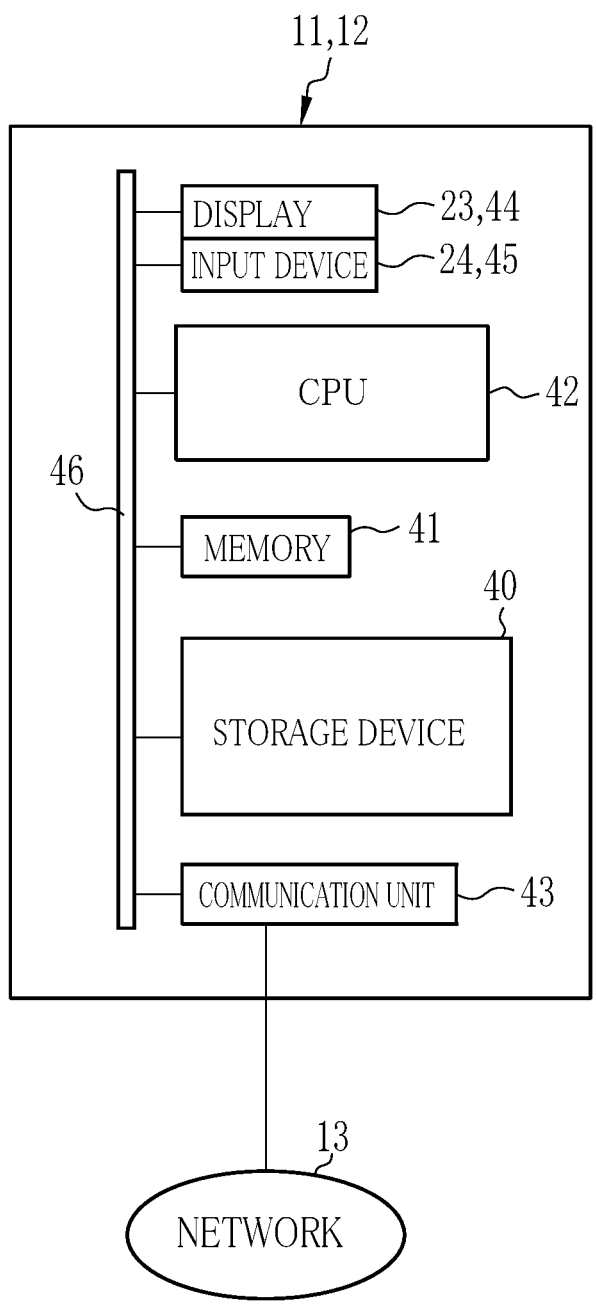
FIG. 9 is a block diagram illustrating a computer constituting the client terminal and the medical examination support server.

In FIG. 9, the computers constituting the client terminal 11 and the medical examination support server 12 have basically the same configuration, and each of the computers includes a storage device 40, a memory 41, a central processing unit (CPU) 42, and a communication unit 43. The client terminal 11 includes the display 23 and the input device 24 as described above, and similarly, the medical examination support server 12 includes a display 44 and an input device 45. These are connected to each other through a data bus 46.

The storage device 40 is a hard disk drive, which is built into a computer that constitutes the client terminal 11 or the like or which is connected to the computer through a cable or a network, or a disk array formed by connecting a plurality of hard disk drives. Control programs such as an operating system, various application programs, and display data of various display screens associated with these programs are stored in the storage device 40.

The memory 41 is a work memory required for the CPU 42 to execute processing. The CPU 42 performs overall control of each unit of the computer by loading a program stored in the storage device 40 to the memory 41 and executing processing according to the program.

The communication unit 43 is a network interface to perform transmission control of various kinds of information through the network 13. The displays 23 and 44 display various display screens according to the operations of the input devices 24 and 45. The display screen has an operation function based on the graphical user interface (GUI). The computer constituting the client terminal 11 or the like receives an input of an operation instruction from the input devices 24 and 45 through the display screen.

In the following description, for the sake of distinction, a suffix "A" is attached to the reference numeral of each unit of the computer constituting the client terminal 11 except for the display 23 and the input device 24, and a suffix "B" is attached to the reference numeral of each unit of the computer constituting the medical examination support server 12 except for the display 44 and the input device 45.

Figure 10:
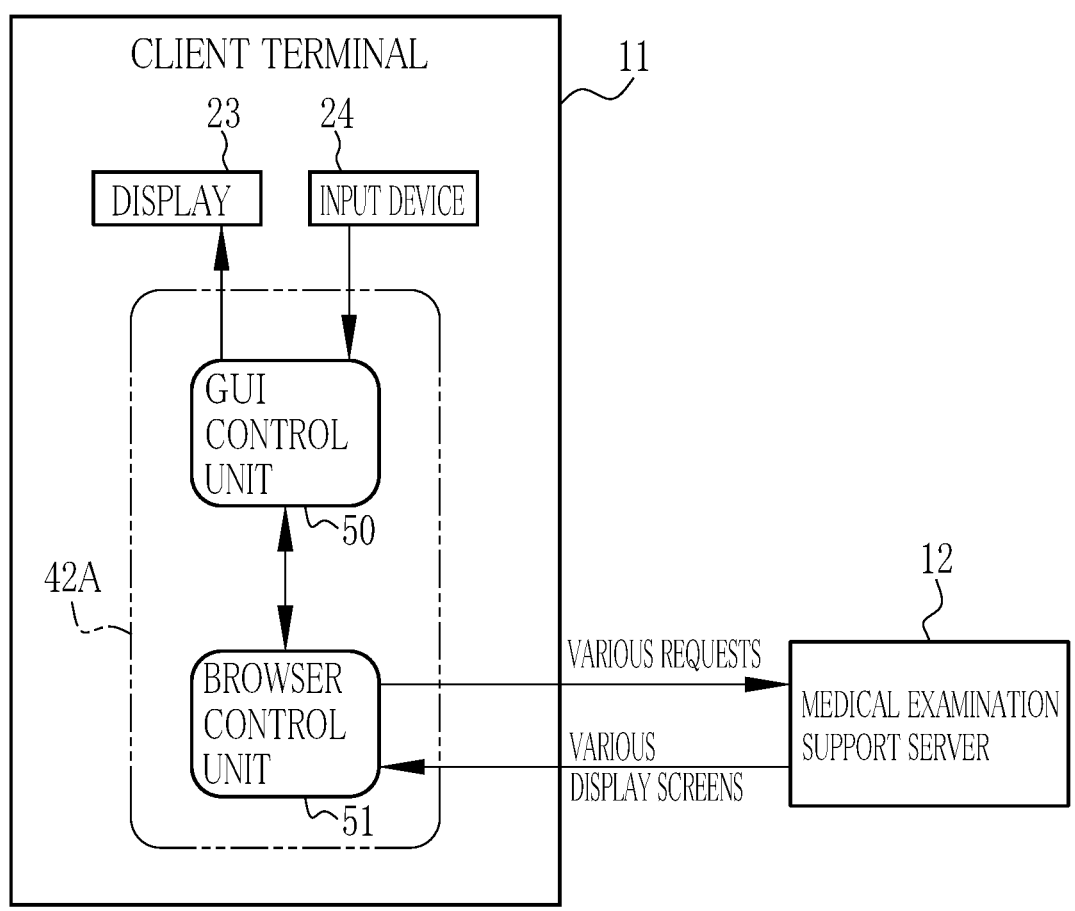
FIG. 10 is a block diagram illustrating various processing units of a CPU of the client terminal.

In FIG. 10, in a case where a web browser is started, the CPU 42A of the client terminal 11 cooperates with the memory 41 or the like to function as a GUI control unit 50 and a browser control unit 51.

The GUI control unit 50 displays various display screens on the display 23, and receives various operation instructions which are input from the input device 24 through various display screens by the medical staff. The operation instructions include a distribution instruction of the integrated display screen 35 to the medical examination support server 12, a registration instruction of the manual operation log MOL, and the like. The GUI control unit 50 outputs the received operation instruction to the browser control unit 51.

The browser control unit 51 controls the operation of the web browser. The browser control unit 51 issues a request according to the operation instruction from the GUI control unit 50, specifically a distribution request for the integrated display screen 35 according to the distribution instruction of the integrated display screen 35, a registration request for the manual operation log MOL according to the registration instruction of the manual operation log MOL to the medical examination support server 12.

The browser control unit 51 receives screen data of each of various display screens from the medical examination support server 12. The browser control unit 51 reproduces the display screen to be displayed on the web browser based on the screen data, and outputs the display screen to the GUI control unit 50. The GUI control unit 50 displays the display screen on the display 23.

Figure 11:
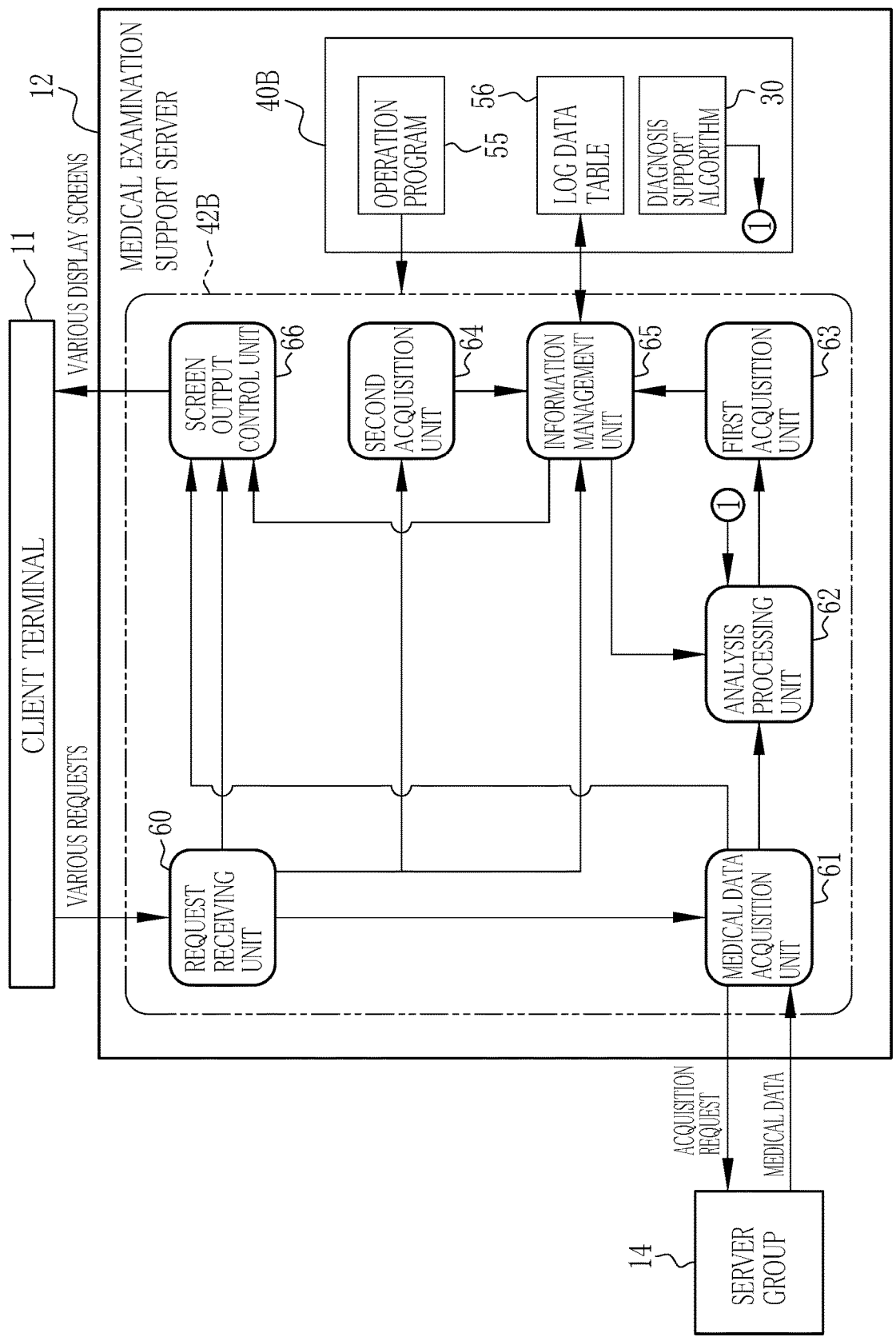
FIG. 11 is a block diagram illustrating various processing units of a CPU of the medical examination support server.

In FIG. 11, the storage device 40B of the medical examination support server 12 stores an operation program 55 in addition to the diagnosis support algorithm 30. The operation program 55 is an application program for causing a computer constituting the medical examination support server 12 to function as a medical examination support apparatus.

A log data table 56 (refer to FIGS. 12 and 13) is also stored in the storage device 40B. The log data table 56 stores examination data in association with the automatic processing log APL and the manual operation log MOL. That is, the storage device 40B corresponds to a storage unit that stores the examination data in association with the automatic processing log APL and the manual operation log MOL.

Although the details are described below, in addition to the automatic processing log APL and the manual operation log MOL, a quotation log QL is also stored in the log data table 56. The quotation log QL is a history in which the diagnosis support information included in the automatic processing log APL or the doctor's analysis result included in the manual operation log MOL is quoted in the medical report 21 or the medical conference.

In a case where the operation program 55 is activated, the CPU 42B of the medical examination support server 12 functions as a request receiving unit 60, a medical data acquisition unit 61, an analysis processing unit 62, a first acquisition unit 63, a second acquisition unit 64, an information management unit 65, and a screen output control unit 66, in cooperation with the memory 41 or the like.

The request receiving unit 60 receives various requests from the client terminal 11. The request receiving unit 60 outputs the distribution request for the integrated display screen 35 to the medical data acquisition unit 61, the information management unit 65, and the screen output control unit 66, and outputs the registration request for the manual operation log MOL to the second acquisition unit 64, among the various requests. The patient ID of the target patient is included in the distribution request for the integrated display screen 35, and the manual operation log MOL is included in the registration request for the manual operation log MOL.

The medical data acquisition unit 61 issues an acquisition request for the medical data of the target patient to the server group 14. In the acquisition request, the patient ID of the target patient included in the distribution request for the integrated display screen 35 from the request receiving unit 60 is the search key. The medical data acquisition unit 61 acquires the medical data of the target patient transmitted from the server group 14 in response to the acquisition request. The medical data acquisition unit 61 outputs the acquired medical data to the analysis processing unit 62 and the screen output control unit 66.

The analysis processing unit 62 executes analysis processing by the diagnosis support algorithm 30. Prior to the execution of the analysis processing, the analysis processing unit 62 selects examination data to be input to the diagnosis support algorithm 30, from the examination data included in the medical data which is from the medical data acquisition unit 61.

More specifically, the analysis processing unit 62 selects examination data which is to be subjected to the analysis processing by the diagnosis support algorithm 30 and for which the diagnosis support information has not been output yet, as examination data to be input to the diagnosis support algorithm 30. The analysis processing unit 62 determines whether the examination data is examination data for which the diagnosis support information has not been output or examination data for which the diagnosis support information has been output, by referring to the automatic processing log APL transferred from the information management unit 65. In a case where, for examination data which is to be subjected to the analysis processing by the diagnosis support algorithm 30, there is an automatic processing log APL associated with the examination data, the analysis processing unit 62 determines that the diagnosis support information has been output, and excludes the examination data from examination data to be input to the diagnosis support algorithm 30.

The analysis processing unit 62 inputs the selected examination data to the diagnosis support algorithm 30, and causes the diagnosis support algorithm 30 to execute analysis processing. In this manner, the analysis processing by the diagnosis support algorithm 30 is automatically executed when the request receiving unit 60 receives a distribution request for the integrated display screen 35. Therefore, it can be said that the distribution request for the integrated display screen 35 is an analysis processing request for the diagnosis support algorithm 30.

The analysis processing unit 62 outputs an automatic processing log APL including the diagnosis support information as the result of the analysis processing to the first acquisition unit 63. In a case where there is no examination data to be input to the diagnosis support algorithm 30, the analysis processing unit 62 does not execute the analysis processing, and also does not output the automatic processing log APL.

The first acquisition unit 63 has a first acquisition function of acquiring an automatic processing log APL from the analysis processing unit 62. The first acquisition unit 63 transfers the acquired automatic processing log APL to the information management unit 65.

The second acquisition unit 64 has a second acquisition function of acquiring a manual operation log MOL included in the registration request for the manual operation log MOL from the request receiving unit 60. The second acquisition unit 64 transfers the acquired manual operation log MOL to the information management unit 65.

The information management unit 65 has an information management function of writing various kinds of information to the storage device 40B and reading various kinds of information from the storage device 40B. The information management unit 65 registers the automatic processing log APL from the first acquisition unit 63 and the manual operation log MOL from the second acquisition unit 64 in the log data table 56. Further, in a case where the diagnosis support information included in the automatic processing log APL or the doctor's analysis result included in the manual operation log MOL is quoted in the medical report 21 or the medical conference, the information management unit 65 registers the quotation log QL in the log data table 56.

The information management unit 65 outputs the automatic processing log APL of the target patient to the analysis processing unit 62 for reference at the time of selecting examination data to be input to the diagnosis support algorithm 30. Further, the information management unit 65 outputs the automatic processing log APL, the manual operation log MOL, and the quotation log QL of the target patient to the screen output control unit 66 in response to the distribution request for the integrated display screen 35 from the request receiving unit 60.

The screen output control unit 66 generates the integrated display screen 35 on the basis of the medical data of the target patient from the medical data acquisition unit 61, and transmits the integrated display screen 35 to the client terminal 11 which is a request source of the distribution request for the integrated display screen 35. Further, the screen output control unit 66 generates a log display screen 95 (refer to FIG. 16) on the basis of the automatic processing log APL, the manual operation log MOL, and the quotation log QL of the target patient from the information management unit 65, and transmits the log display screen 95 to the client terminal 11 which is a request source of the distribution request for the integrated display screen 35. That is, the screen output control unit 66 has a screen output control function of controlling the output of the log display screen 95. Further, since the log display screen 95 is also transmitted in response to the distribution request for the integrated display screen 35, the distribution request for the integrated display screen 35 is a distribution request for the log display screen 95.

Figure 12:
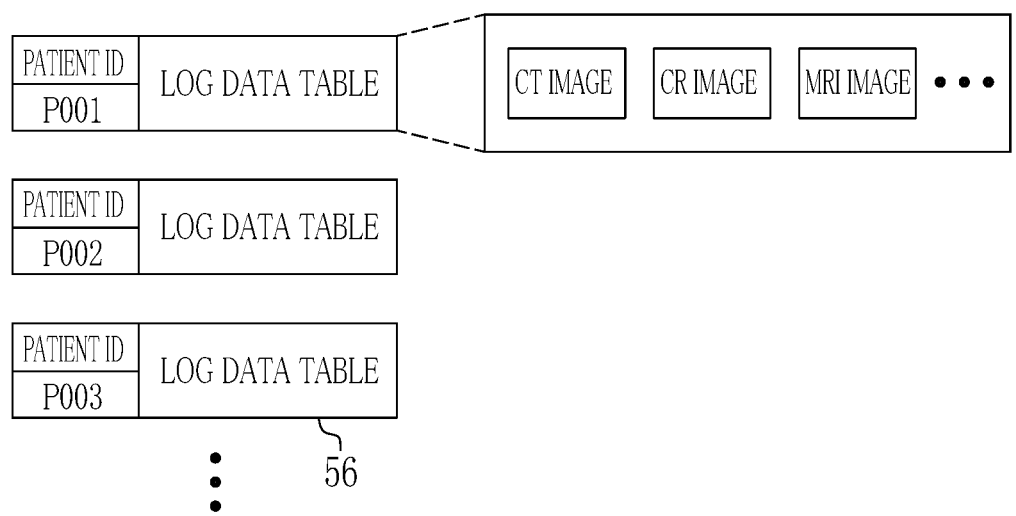
FIG. 12 is a diagram illustrating contents of log data tables.

In FIG. 12, the log data table 56 is managed for each patient as in case of the electronic medical record 19, the medical image 20, and the like. The log data table 56 is prepared for each medical image 20 such as a CT image, a CR image, and an MRI image.

FIG. 13 illustrates the log data table 56 relating to CT images of a patient having a patient ID of P001. The log data table 56 has items of a log ID, registration date and time, an algorithm ID, a staff ID, an image ID, a quotation source and a quotation destination, contents, diagnosis support information, a doctor's analysis result, display state information, presence/absence of detailed information display, and the number of times of quotation.

The log ID is a symbol and a number for identifying each log. The log ID is automatically assigned by the information management unit 65 at the time of registering each log in the log data table 56. APL, MOL, and QL are respectively assigned as symbols to the log ID of the automatic processing log APL, the log ID of the manual operation log MOL, and the log ID of the quotation log QL, and numbers are assigned thereafter in order.

In the item of the registration date and time, date and time at which the information management unit 65 registers each log in the log data table 56 is recorded. In the item of the algorithm ID, an algorithm ID of the diagnosis support algorithm 30 which executes the analysis processing relating to the automatic processing log APL is recorded. Therefore, the algorithm ID is recorded only in the automatic processing log APL, and is not recorded in the manual operation log MOL and the quotation log QL.

In the item of the staff ID, a staff ID of the medical staff who performed the manual operation relating to the manual operation log MOL or the quotation act relating to the quotation log QL is registered. Therefore, the staff ID is not recorded in the automatic processing log APL.

In the item of the image ID, an image ID of the CT image as the target of each log is recorded. In the item of the quotation source and the quotation destination, a log ID of the automatic processing log APL or the manual operation log MOL which is a quotation source relating to the quotation log QL, and a report ID of the medical report 21 or a conference ID of the medical conference which is a quotation destination are recorded. Therefore, the quotation source and the quotation destination are recorded only in the quotation log QL, and are not recorded in the automatic processing log APL and the manual operation log MOL.

In the item of the contents, specific contents of each log are recorded. For example, in the automatic processing log APL having a log ID of APL001, extraction of a lesion, identification of the type of a lesion, and measurement of the size of a lesion are recorded. In the manual operation log MOL having a log ID of MOL001, an enlarged display operation is recorded. Further, in the manual operation log MOL having a log ID of MOL002, a lesion measurement operation is recorded.

The diagnosis support information is recorded in the item of the diagnosis support information, and the doctor's analysis result is recorded in the item of the doctor's analysis result. The diagnosis support information is recorded only in the automatic processing log APL, and the doctor's analysis result is recorded in the manual operation log MOL accompanying the doctor's analysis result such as a lesion measurement operation.

The display state information is recorded in the item of the display state information. The display state information is information representing a display state of the examination data that the doctor was viewing at the time of acquisition of the manual operation log MOL. The display state information is, in short, a screenshot of the display 23 at the time of acquisition of the manual operation log MOL. The display state information is recorded only in the manual operation log MOL.

In the item of the presence/absence of detailed information display, whether to display detailed information of the automatic processing log APL is recorded. That is, in case of displaying the detailed information, "displayed" is recorded, and in case of not displaying the detailed information, "not displayed" is recorded as illustrated in the drawing. The presence/absence of detailed information display is registered for each medical staff. The detailed information is the name of the diagnosis support algorithm 30 executing the analysis processing, the diagnosis support information, and the like.

In the item of the number of times of quotation, the number of times of quotation of the diagnosis support information included in the automatic processing log APL or the doctor's analysis result included in the manual operation log MOL in the medical report 21 or the medical conference is recorded. More specifically, the number of quotation logs QL in which the log ID is recorded as the quotation source is totalized for each of the automatic processing log APL and the manual operation log MOL, and the totalized number is registered as the number of times of quotation.

The followings can be known from the log data table 56 illustrated in FIG. 13. First, from the automatic processing log APL having a log ID of APL001, it can be known that analysis processing of extraction of a lesion, identification of the type of a lesion, and measurement of the size of a lesion is executed on a CT image having an image ID of CT050-5 by the diagnosis support algorithm 30 having an algorithm ID of AL050, and diagnosis support information indicating the lesion position (X, Y), the type A, and the size of 10×5 mm and 300 mm$^3$ is output. Further, it can be known that the detailed information of the automatic processing log APL is not displayed yet, and the diagnosis support information is not quoted in the medical report 21 or the medical conference.

Next, from the manual operation logs MOL having log IDs of MOL001 and MOL002, it can be known that an enlarged display operation and a lesion measurement operation are performed on a CT image having an image ID of CT050-5 by a doctor having a staff ID of SF050, and the lesion measurement result of the lesion position (XX, YY), the type A, and the size of 11×6 mm and 330 mm$^3$ is output.

Then, from the quotation log QL having a log ID of QL001, it can be known that the doctor's analysis result included in the manual operation log MOL having a log ID of MOL002 is quoted in the medical report 21 having a report ID of RE050 by a doctor having a staff ID of SF060.

The medical staff accesses the medical examination support server 12 via the client terminal 11, and performs authentication by inputting his/her own staff ID and an authentication key. The staff ID input at this time is recorded in the item of the staff ID of the log data table 56.

After authentication, an input screen for the patient ID is displayed on the web browser of the display 23 of the client terminal 11. In the input screen for the patient ID, for example, an input box for the patient ID, and a transmission button for performing a distribution instruction of the integrated display screen 35 are prepared. In a case where a patient ID of the target patient is input to the input box and the transmission button is selected, a distribution request for the integrated display screen 35 including a patient ID of the target patient is issued from the browser control unit 51 of the client terminal 11 to the request receiving unit 60 of the medical examination support server 12.

The distribution request for the integrated display screen 35 is received, and the acquisition request is issued from the medical data acquisition unit 61 to the server group 14. The server group 14 transmits the medical data such as the electronic medical record 19 and the medical image 20 to which the patient ID of the target patient is assigned, to the medical data acquisition unit 61. The screen output control unit 66 generates the integrated display screen 35 illustrated in FIG. 14 on the basis of the medical data of the target patient from the server group 14.

In FIG. 14, the integrated display screen 35 is divided into roughly four display regions of a first display region 70, a second display region 71, a third display region 72, and a fourth display region 73. In the first display region 70, a graph indicating a time-series change of a measurement value of each measurement item such as the body temperature, pulse, and blood pressure (high and low) of vital signs, a bar indicating a dosage and an administration period of the medicine, and the like are displayed.

In the second display region 71, a plurality of windows displaying the medical data are displayed side by side. For example, measurement values of a plurality of measurement items of the blood test are displayed in a list in a certain window, and measurement values of a plurality of measurement items of the urine test are displayed in a list in a certain window. Further, there is a window in which the type and the dosage of the medicine are displayed in a list. There are windows in which a thumbnail 75 of each of various medical images 20 is displayed, as three windows arranged on a right end of the second display region 71. The latest medical data is displayed in each window of the second display region 71.

In the second display region 71, a window of a creation application program of the medical report 21 (hereinafter, referred to as report window) 76, a window of a creation application program of the conference information 22 (hereinafter, referred to as conference window) 77, and a window of various application programs are displayed.

In the third display region 72, patient information of the target patient, such as the patient ID, the name, gender, age, date of birth, preference, past illness, and allergies, and the affiliation medical department and the name of the attending physician of the target patient are displayed. In the fourth display region 73, windows displaying the patient's chief complaint, the consultation record, the nursing record, and the information from the patient's family included in the electronic medical record 19 are displayed side by side. In the window displayed in the fourth display region 73, the annotation input operation and the diagnosis name input operation can be performed. The annotation is the doctor's impression for the patient's chief complaint, for example.

The thumbnail 75 of the medical image 20 in the second display region 71 can be selected by a cursor 80. In a case where the thumbnail 75 is selected by the cursor 80, the screen output control unit 66 causes a viewer screen 85 illustrated in FIG. 15 to be displayed in a pop-up on the integrated display screen 35.

In FIG. 15, the viewer screen 85 includes an image display region 86 in which a full-size medical image 20 is displayed, an information display region 87 in which the patient information such as the patient ID and the additional information such as the patient's name, the imaging date and time, the imaging part, and the direction are displayed, and a measurement result input region 88 in which the lesion measurement result such as the type of a lesion and the size of a lesion is input.

In the viewer screen 85, a full-size medical image 20 is displayed instead of the thumbnail 75 in the integrated display screen 35. Accordingly, the operation of selecting the thumbnail 75 in the integrated display screen 35 by the cursor 80 corresponds to the enlarged display operation of the medical image 20. Therefore, in a case where the thumbnail 75 is selected in the integrated display screen 35, the browser control unit 51 issues the registration request for the manual operation log MOL including the image ID or the like, to the request receiving unit 60. That is, the selection of the thumbnail 75 corresponds to the registration instruction of the manual operation log MOL. In this case, the information management unit 65 registers the enlarged display operation in the item of contents of the manual operation log MOL.

In the viewer screen 85, a lesion in the medical image 20 can be designated. The designation of a lesion is performed by inputting a plurality of control points to surround the periphery of a region seemed to be a lesion in the medical image 20 in the image display region 86 by the cursor 80. A frame 89 indicated by a dashed line that draws a smooth curve passing through the plurality of control points and an inside of the frame 89 are designated as a lesion.

The doctor designates a lesion, inputs the type and size of the lesion to the measurement result input region 88, and then selects a registration button 90 by the cursor 80. The operation of selecting the registration button 90 corresponds to the lesion measurement operation. Therefore, in a case where the registration button 90 is selected, the browser control unit 51 issues the registration request for the manual operation log MOL including the lesion measurement result, the image ID, or the like, to the request receiving unit 60. That is, the selection of the registration button 90 also corresponds to the registration instruction of the manual operation log MOL. In this case, the information management unit 65 registers the lesion measurement operation in the item of contents of the manual operation log MOL, and registers the lesion measurement result in the item of the doctor's analysis result.

In a case where a plurality of lesions are present in the medical image 20, designating the frame 89 and inputting the type and size are performed for each lesion. The browser control unit 51 issues the registration request for the manual operation log MOL to the request receiving unit 60 each time the registration button 90 is selected for each lesion. Therefore, in a case where a plurality of lesions are present in the medical image 20, the second acquisition unit 64 acquires the manual operation log MOL relating to the lesion measurement operation of each of the plurality of lesions.

In the viewer screen 85, in addition to the enlarged display operation and the lesion measurement operation described above, the comparison display operation and the annotation input operation can be performed. The comparison display operation is specifically an instruction of displaying the medical image 20 obtained in the previous image examination and the medical image 20 obtained in the current image examination in parallel, or the like. Further, the annotation in this case is doctor's impression for the lesion.

The registration request for the manual operation log MOL may be issued by one action such as selecting a registration instruction button on the integrated display screen 35 by the cursor 80 or pressing a print screen button of the keyboard. For example, in a case where the registration instruction button or the print screen button is selected in a state where the viewer screen 85 of the CT image, the MRI image, and the ECG image is displayed, the registration request for the manual operation log MOL collectively including the enlarged display operations of the respective images is issued. In this manner, the medical staff can register the manual operation log MOL at his/her preferred timing.

Figure 16:
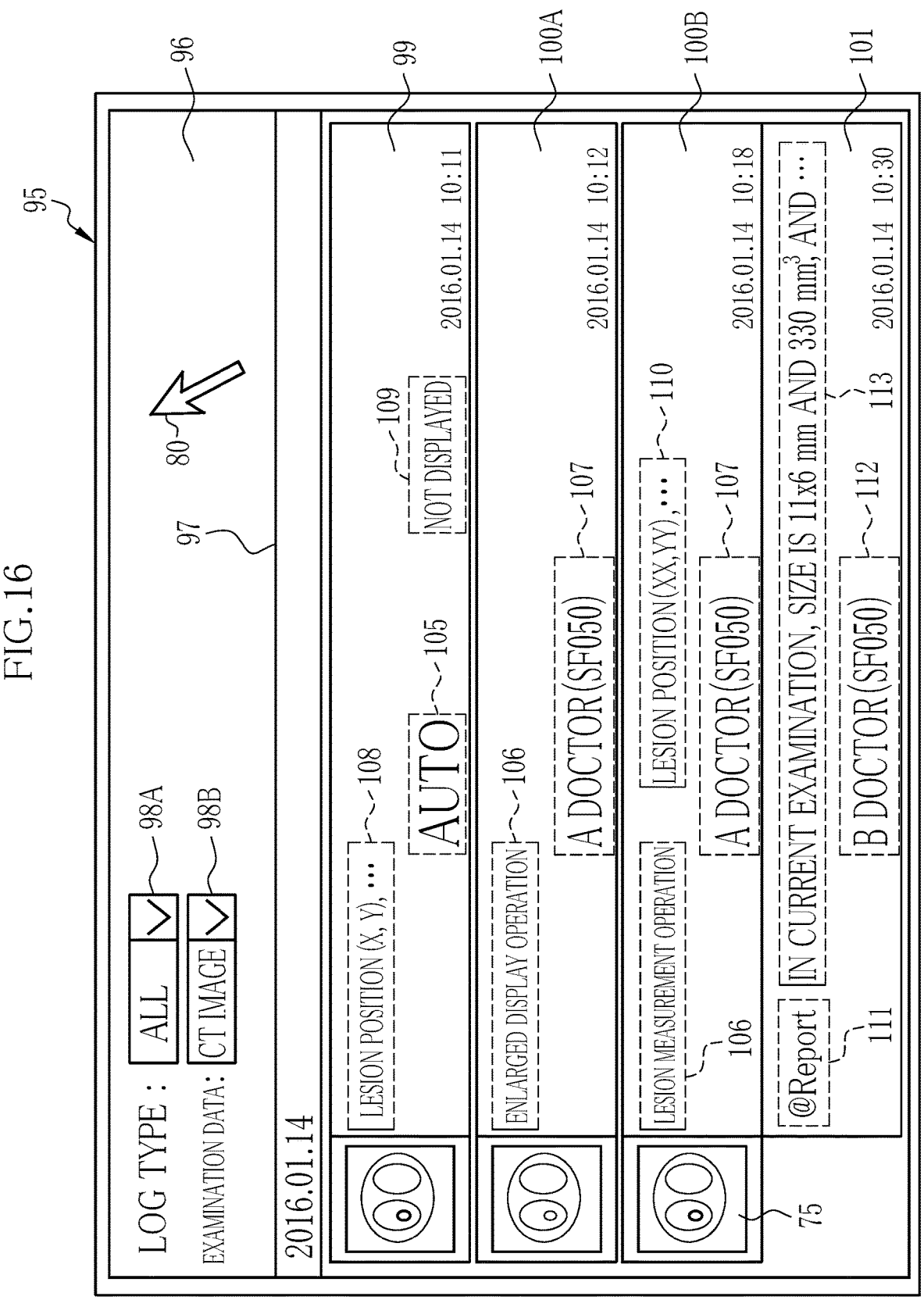
FIG. 16 is a diagram illustrating a log display screen.

The screen output control unit 66 causes the log display screen 95 illustrated in FIG. 16 to be displayed on a lower portion of the integrated display screen 35 or the like.

In FIG. 16, the log display screen 95 has a display selection region 96 and a collective display region 97. The display selection region 96 is provided with two pull-down menus 98A and 98B. The pull-down menu 98A is for selecting the type of logs to be displayed in the collective display region 97. In the pull-down menu 98A, options for displaying only the automatic processing log APL, only the manual operation log MOL, or only the quotation log QL are prepared in addition to an option of "all" for displaying all types of logs, which is illustrated in the drawing. The pull-down menu 98B is for narrowing down the logs to be displayed in the collective display region 97 using the examination data. In the pull-down menu 98B, an option of "all" for displaying logs relating to all of the examination data, and options for displaying only the log relating to the CR image or only the log relating to the MRI image are prepared in addition to an option of "CT image" for displaying only the log relating to the CT image, which is illustrated in the drawing. In a case where the log display screen 95 is displayed, the option of "all" is selected in each of the pull-down menus 98A and 98B. In addition to this, a pull-down menu for narrowing down the logs to be displayed in the collective display region 97 using the date, the imaging part, the direction, or the like may be provided.

In the collective display region 97, display based on the registration contents of the log data table 56 is performed. That is, in the collective display region 97, a display block of the automatic processing log APL (hereinafter, referred to as APL block) 99, and a display block of the manual operation log MOL (hereinafter, referred to as MOL block) 100 are collectively displayed. Further, in the collective display region 97, a display block of the quotation log QL (hereinafter, referred to as QL block) 101 is also displayed. In the APL block 99 and the MOL block 100, the thumbnail 75 of the medical image 20 is displayed as in case of the windows in the second display region 71 of the integrated display screen 35. In FIG. 16, the log display screen 95 in which the display based on the registration contents of the log data table 56 relating to the CT image of the patient having a patient ID of P001 illustrated in FIG. 13 is performed is illustrated.

The APL block 99 and the MOL block 100 are displayed in time series. In FIG. 16, from the top to the bottom, the APL block 99 and the MOL block 100 are arranged in an ascending order of registration date and time. That is, when the APL block 99 and the MOL block 100 in the collective display region 97 are viewed in order from the top, it can be known that in what order the automatic processing and the manual operation were performed.

In FIG. 16, the APL block 99 and the MOL block 100 for one day of "2016.01.14" are displayed, but in a case where there are a plurality of consultation dates of the target patient, the APL block 99 and the MOL block 100 for a plurality of days are displayed. In this case, the collective display region 97 is divided into small regions for each day.

In the APL block 99, as indicated by a frame with a broken line and reference numeral 105, characters (AUTO) indicating deriving from the automatic processing of the diagnosis support algorithm 30 are written. On the other hand, in the MOL block 100, as indicated by frames with broken lines and reference numerals 106 and 107, characters (enlarged display operation in MOL block 100A, lesion measurement operation in MOL block 100B) indicating specific contents of the manual operation, and characters (A doctor (SF050)) indicating the medical staff who performed the manual operation and the staff ID thereof are written. The APL block 99 and the MOL block 100 can be distinguishable from each other by such character notations 105 to 107.

As a method of displaying the APL block 99 and the MOL block 100 in a distinguishable manner, instead of or in addition to the method of varying the character notations, a method of changing the character style (bold, italic, underline, font, and the like) between the APL block 99 and the MOL block 100, changing the background color between the APL block 99 and the MOL block 100 (gray in the APL block 99, light blue in the MOL block 100), surrounding any of the APL block 99 and the MOL block 100 with a frame, or graying out any of the APL block 99 and the MOL block 100 may be adopted.

In the APL block 99, as indicated by a frame with a broken line and reference numeral 108, characters indicating a part of the diagnosis support information is written. Further, in the APL block 99, as indicated by a frame with a broken line and reference numeral 109, characters indicating whether the detailed information has been displayed or has not been displayed are written. In case of FIG. 16, characters (not displayed) indicating that the detailed information has not been displayed are written.

In the MOL block 100B of the lesion measurement operation, as indicated by a frame with a broken line and reference numeral 110, characters indicating a part of the lesion measurement result are written.

The screen output control unit 66 causes the QL block 101 to be displayed to correspond to the APL block 99 of the automatic processing log APL as the quotation source or the MOL block 100 of the manual operation log MOL as the quotation source, in the collective display region 97. More specifically, the QL block 101 is displayed to be hung down right below the APL block 99 of the automatic processing log APL as the quotation source or the MOL block 100 of the manual operation log MOL as the quotation source. FIG. 16 illustrates an example in which the manual operation log MOL of the MOL block 100B is the quotation source and the QL block 101 is displayed right below the MOL block 100B.

In the QL block 101, as indicated by a frame with a broken line and reference numeral 111, characters (@Report) indicating the quotation destination of the diagnosis support information included in the automatic processing log APL or the doctor's analysis result included in the manual operation log MOL are written. The characters "@Report" exemplified here indicate that the quotation destination of the diagnosis support information or the doctor's analysis result is the medical report 21. In a case where the medical conference is the quotation destination, instead of @Report, characters of @Conference (refer to reference numeral 157 of FIG. 27 or the like) are written.

In the QL block 101, similar to the MOL block 100, as indicated by a frame with a broken line and reference numeral 112, characters (B doctor (SF060)) indicating the medical staff who performed the quotation act and the staff ID thereof are written. Further, in the QL block 101, as indicated by a frame with a broken line and reference numeral 113, characters indicating a part of the contents of the medical report 21 or the medical conference which is the quotation destination are written.

In a case where the number of APL blocks 99, MOL blocks 100, and QL blocks 101 reach a number that cannot be displayed at one time, a vertical scroll bar is displayed in the collective display region 97.

As a method of quoting the diagnosis support information or the doctor's analysis result in the medical report 21 or the medical conference, an aspect illustrated in FIG. 17 is adopted, for example. That is, the APL block 99 or the MOL block 100 in the collective display region 97 is dragged and dropped into the report window 76 or the conference window 77. The screen output control unit 66 causes the QL block 101 to be displayed right below the APL block 99 or the MOL block 100 which has been dragged and dropped. FIG. 17 illustrates an aspect in which the MOL block 100B of the lesion measurement operation illustrated in FIG. 16 is dragged and dropped into the report window 76 and the QL block 101 is displayed right below the MOL block 100B.

Figure 18A:
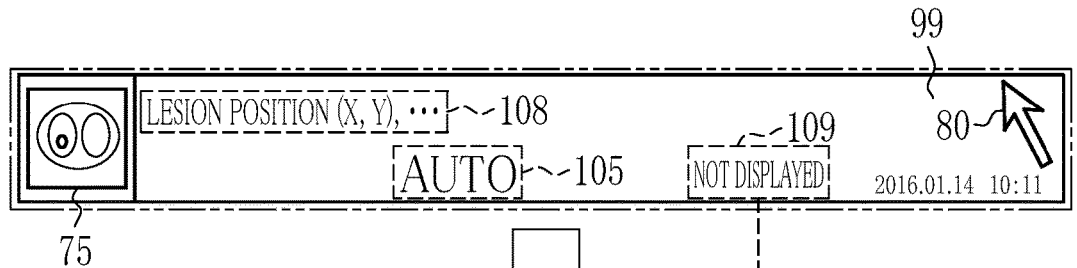
FIG. 18A illustrates a display block of an automatic processing log before a selection instruction.
Figure 18B:
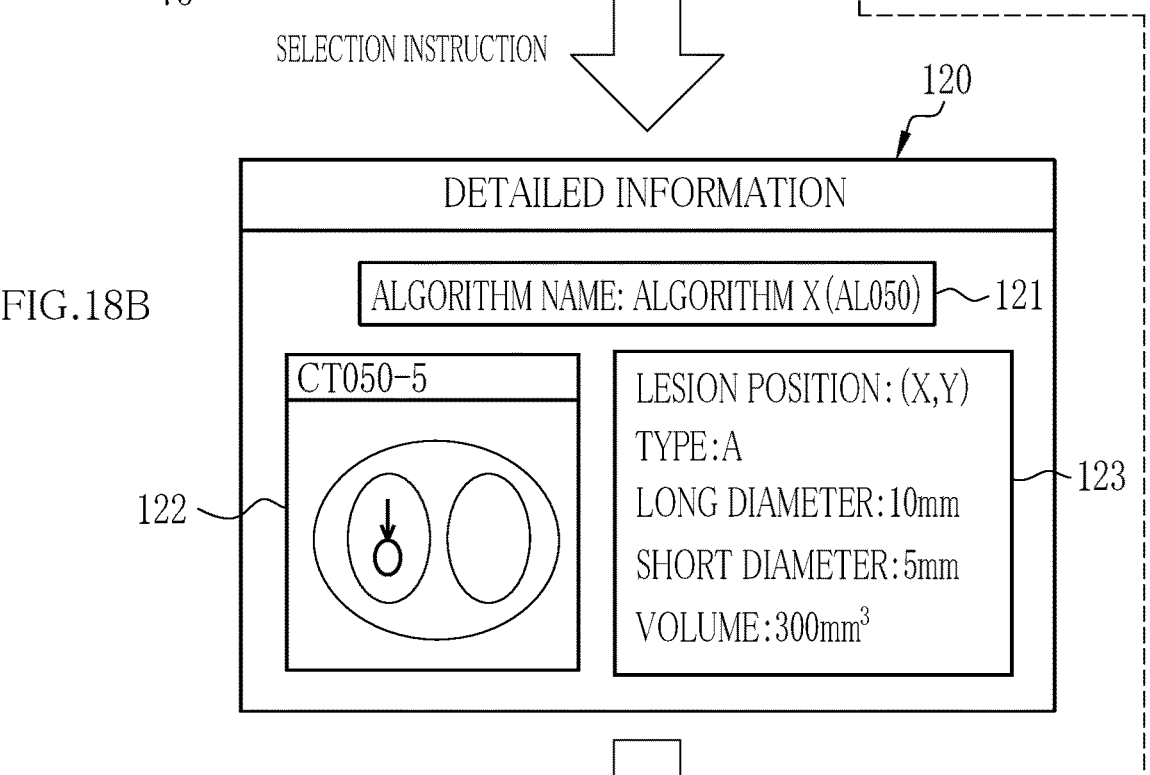
FIG. 18B illustrates a detailed information display screen.

As illustrated in FIG. 18A, in the collective display region 97, the APL block 99 receives a selection instruction by the cursor 80. In a case where there is a selection instruction of the APL block 99 by the cursor 80, the screen output control unit 66 causes a detailed information display screen 120 illustrated in FIG. 18B to be displayed in a pop-up on the log display screen 95.

The detailed information display screen 120 has an algorithm display region 121 in which the name of the diagnosis support algorithm 30 executing the automatic processing or the like is displayed, an image display region 122 in which the medical image 20 is displayed, and a diagnosis support information display region 123 in which the diagnosis support information is displayed. In the medical image 20 in the image display region 122, a frame and an arrow indicating the position of a lesion extracted in the diagnosis support algorithm 30 are displayed. The display of the detailed information display screen 120 disappears by clicking a right button of the mouse or pressing an escape key on the keyboard.

Figure 18C:
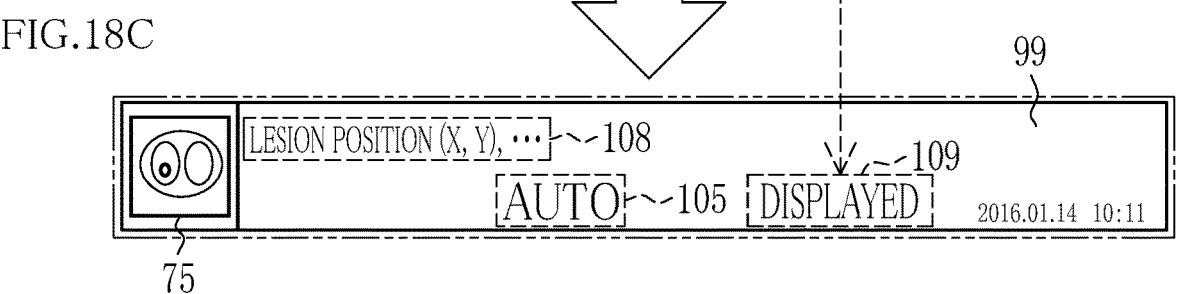
FIG. 18C illustrates a display block of an automatic processing log after a selection instruction.

The screen output control unit 66 causes "not displayed" to be displayed in the character notation 109 in the APL block 99 before the selection instruction illustrated in FIG. 18A since the detailed information has not been displayed. In contrast, in the APL block 99 illustrated in FIG. 18C after the selection instruction is performed and the detailed information display screen 120 is displayed, "displayed" indicating that the detailed information has been displayed is displayed in the character notation 109. The screen output control unit 66 varies the display aspect between the automatic processing log APL of which the selection instruction has been received and the detailed information has been displayed, and the automatic processing log APL of which the selection instruction has not been received and the detailed information has not been displayed, by switching the display of the character notation 109.

Figure 19A:
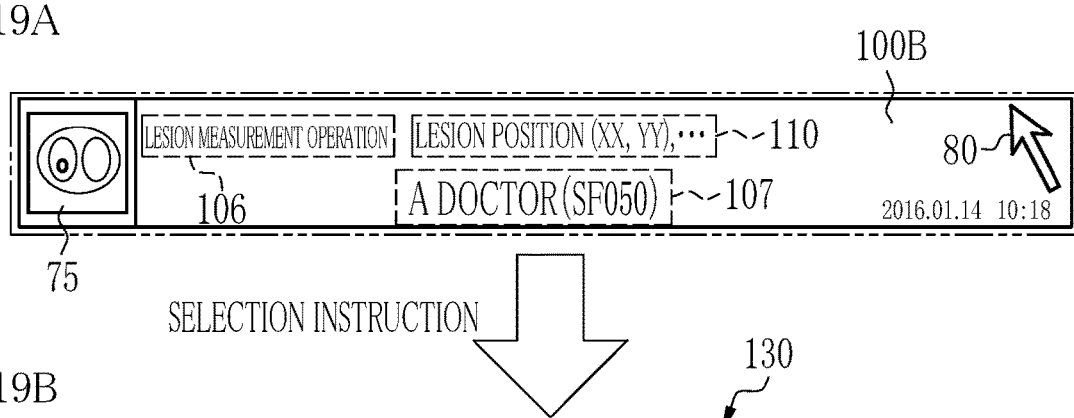
FIG. 19A illustrates a display block of the manual operation log.

As illustrated in FIG. 19A, in the collective display region 97, the MOL block 100 also receives a selection instruction by the cursor 80. In a case where there is a selection instruction of the MOL block 100 by the cursor 80, the screen output control unit 66 causes a reproduction screen 130, in which the display state of the examination data of the manual operation log MOL relating to the MOL block 100 which has received the selection instruction is reproduced on the basis of the display state information of the log data table 56, to be displayed in a pop-up on the log display screen 95 as illustrated in FIG. 19B.

Figure 19B:
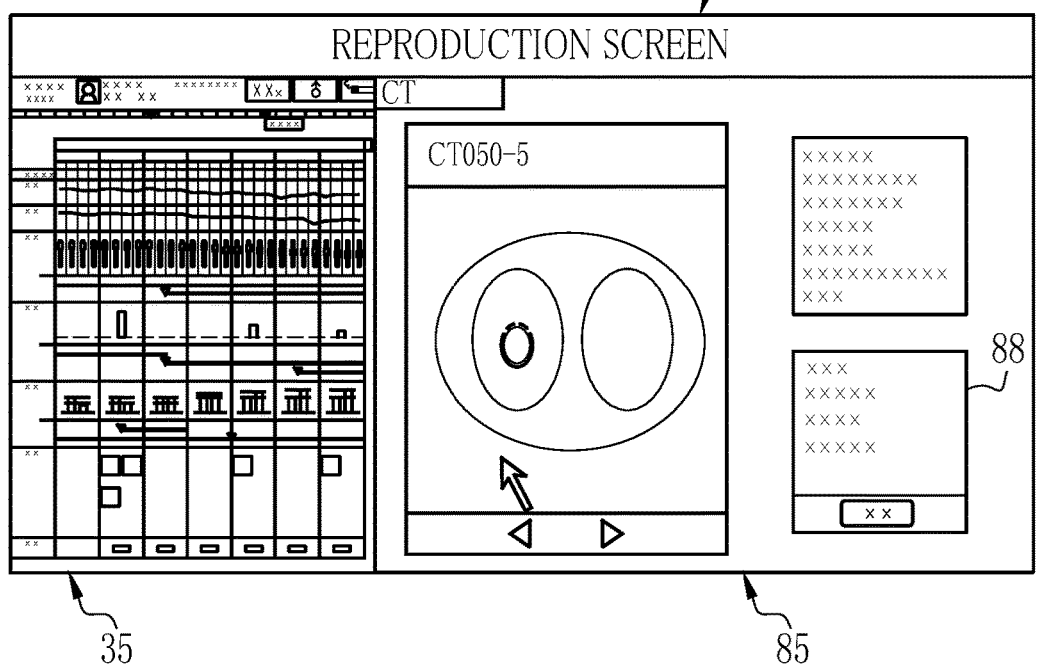
FIG. 19B illustrates a reproduction screen of the display state.

FIG. 19 illustrates a case in which the selection instruction of the MOL block 100B of the lesion measurement operation illustrated in FIG. 16 is received. In this case, the screen output control unit 66 causes the viewer screen 85 to be displayed in a pop-up on the integrated display screen 35 as illustrated in FIG. 19B, and the reproduction screen 130 of a state in which the lesion measurement result is input to the measurement result input region 88 in the viewer screen 85 is displayed. Similar to the detailed information display screen 120, the display of the reproduction screen 130 disappears by clicking a right button of the mouse or pressing an escape key on the keyboard.

Hereinafter, the operation of the above configuration will be described with reference to the flowcharts in FIGS. 20 and 21. First, the medical staff such as a doctor accesses the medical examination support server 12 via the client terminal 11, and performs authentication. In this case, the medical staff inputs his/her own staff ID and an authentication key. After authentication, in the medical examination support server 12, the request receiving unit 60 receives various requests from the client terminal 11.

In FIG. 20, in a case where the distribution request for the integrated display screen 35 is received by the request receiving unit 60 (YES in step ST100), an acquisition request for the medical data of the target patient is issued from the medical data acquisition unit 61 to the server group 14. The medical data of the target patient transmitted from the server group 14 in response to the acquisition request is acquired by the medical data acquisition unit 61 (step ST110).

The analysis processing unit 62 determines whether there is examination data for which the diagnosis support information has not been output, among the medical data of the target patient. In a case where there is examination data for which the diagnosis support information has not been output (YES in step ST120), the corresponding examination data is input to the diagnosis support algorithm 30 by the analysis processing unit 62, and the analysis processing is executed (step ST130). An automatic processing log APL including the diagnosis support information as the result of the analysis processing is output from the analysis processing unit 62 to the first acquisition unit 63. In this manner, the automatic processing log APL is acquired by the first acquisition unit 63 (step ST140, first acquisition step). The automatic processing log APL is transferred from the first acquisition unit 63 to the information management unit 65, and is registered in the log data table 56 by the information management unit 65 (step ST150, information management step). In a case where there is no examination data for which the diagnosis support information has not been output (NO in step ST120), processing of steps ST130 to ST150 is not performed.

In a case where a registration request for a manual operation log MOL is received by the request receiving unit 60 (YES in step ST160), the manual operation log MOL included in the registration request is acquired by the second acquisition unit 64 (step ST170, second acquisition step). The manual operation log MOL is transferred from the second acquisition unit 64 to the information management unit 65, and is registered in the log data table 56 by the information management unit 65 (step ST180, information management step).

Figure 21:
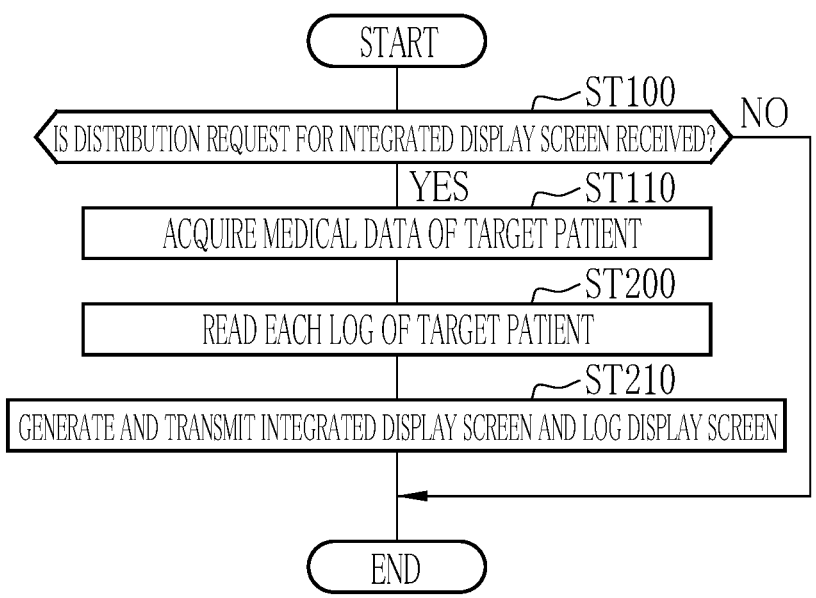
FIG. 21 is a flowchart illustrating a processing procedure of a medical examination support server.

FIG. 20 illustrates a flowchart following a processing procedure of the medical examination support server 12 mainly from the viewpoint of the first acquisition unit 63 and the second acquisition unit 64, and FIG. 21 illustrates a flowchart following a processing procedure of the medical examination support server 12 mainly from the viewpoint of the screen output control unit 66.

The distribution request for the integrated display screen 35 is received by the request receiving unit 60 (YES in step ST100), and the medical data which is acquired by the medical data acquisition unit 61 in step ST110 in response to the reception of the distribution request is output to the screen output control unit 66. Further, each log of the target patient is read from the log data table 56 by the information management unit 65, and is output to the screen output control unit 66 (step ST200).

In the screen output control unit 66, the integrated display screen 35 is generated on the basis of the medical data of the target patient from the medical data acquisition unit 61. The log display screen 95 is generated on the basis of each log of the target patient from the information management unit 65. The generated integrated display screen 35 and log display screen 95 are transmitted to the client terminal 11 which is a request source of the distribution request (step ST210, screen output control step).

In the client terminal 11 which is a request source of the distribution request for the integrated display screen 35, the integrated display screen 35 and the log display screen 95 from the medical examination support server 12 are displayed on the display 23.

In a case where a thumbnail 75 of the medical image 20 in the integrated display screen 35 is selected, the viewer screen 85 is displayed in a pop-up on the integrated display screen 35 by the screen output control unit 66. Further, in this case, the registration request for the manual operation log MOL (enlarged display operation) is issued from the browser control unit 51, and is received by the request receiving unit 60.

Even in a case where the lesion measurement result is input to the measurement result input region 88 in the viewer screen 85 and the registration button 90 is selected, the registration request for the manual operation log MOL (lesion measurement operation) is issued from the browser control unit 51, and is received by the request receiving unit 60.

In this manner, the manual operation log MOL is registered frequently even after the transmission of the integrated display screen 35 and the log display screen 95 in step ST210 of FIG. 21. In a case where a timing at which the analysis processing (step ST130 of FIG. 20) of the diagnosis support algorithm 30 is ended is after the transmission of the integrated display screen 35 and the log display screen 95 in step ST210 of FIG. 21, the automatic processing log APL is also registered after the transmission of the integrated display screen 35 and the log display screen 95 in step ST210 of FIG. 21. The screen output control unit 66 updates the display of the log display screen 95 each time the automatic processing log APL and the manual operation log MOL are newly registered.

In the collective display region 97 in the log display screen 95, the APL block 99 and the MOL block 100 are collectively displayed in a time series in a distinguishable manner. Therefore, it can be clearly known whether a certain manual operation is executed before the output of the diagnosis support information or is executed after the output of the diagnosis support information. Accordingly, it is possible to easily grasp the history of doctor's diagnosis at a glance.

For example, in a case where a manual operation accompanying the doctor's analysis result is executed before the output of the diagnosis support information, the possibility that the doctor has derived the analysis result without referring to the diagnosis support information much is high. In contrast, in a case where a manual operation accompanying the doctor's analysis result is executed after the output of the diagnosis support information, the possibility that the doctor has derived the analysis result based on the diagnosis support information is high. In a case where the history of the diagnosis can be easily grasped in this manner, for example, the time required when the doctor reviews the history of his/her own diagnosis or when the supervisor reviews the history of the doctor's diagnosis becomes short, which is efficient.

Further, it can be known that what kind of manual operations or quotation acts is executed by which medical staff, by the MOL block 100 and the QL block 101 at a glance. Therefore, it is possible for a manager who is in charge of the entire medical facility to grasp the approximate work status of each medical staff by viewing the collective display region 97.

In the collective display region 97, in addition to the APL block 99 and the MOL block 100, the QL block 101 is also displayed. Further, the QL block 101 is displayed to correspond to the APL block 99 of the automatic processing log APL as the quotation source or the MOL block 100 of the manual operation log MOL as the quotation source. Therefore, it can be known that what kind of diagnosis support information or doctor's analysis result is quoted in which medical report 21 or medical conference at a glance.

As illustrated in FIG. 18, the display aspect is varied between the APL block 99 of the automatic processing log APL of which the detailed information including the diagnosis support information has been displayed, and the APL block 99 of the automatic processing log APL of which the detailed information has not been displayed, and thus it can be known that whether the medical staff has checked the diagnosis support information by the display of the detailed information at a glance. Therefore, even in a case where a manual operation accompanying the doctor's analysis result is executed after the output of the diagnosis support information, when the detailed information is not displayed and the diagnosis support information is not checked, it can be determined that the doctor has derived the analysis result without referring to the diagnosis support information.

It is considered that the automatic processing log APL of which the detailed information is not displayed even when some time has passed from the initial display is information which is less important for the doctor. Thus, for the automatic processing log APL of which the detailed information is not displayed even when a preset display period has passed, the APL block 99 may be automatically grayed out or may not be automatically displayed. Similarly, for the automatic processing log APL of which the number of times of quotation is zero even when a preset display period has passed, the APL block 99 may be automatically grayed out or may not be automatically displayed.

As illustrated in FIG. 19, by reproducing the display state of the examination data of the manual operation log MOL of which the selection instruction has been received, on the basis of the display state information representing the display state of the examination data that the doctor was viewing at the time of acquisition of the manual operation log MOL, it is possible to easily grasp in what display state the doctor has performed the manual operation.

Second Embodiment

Figure 22:
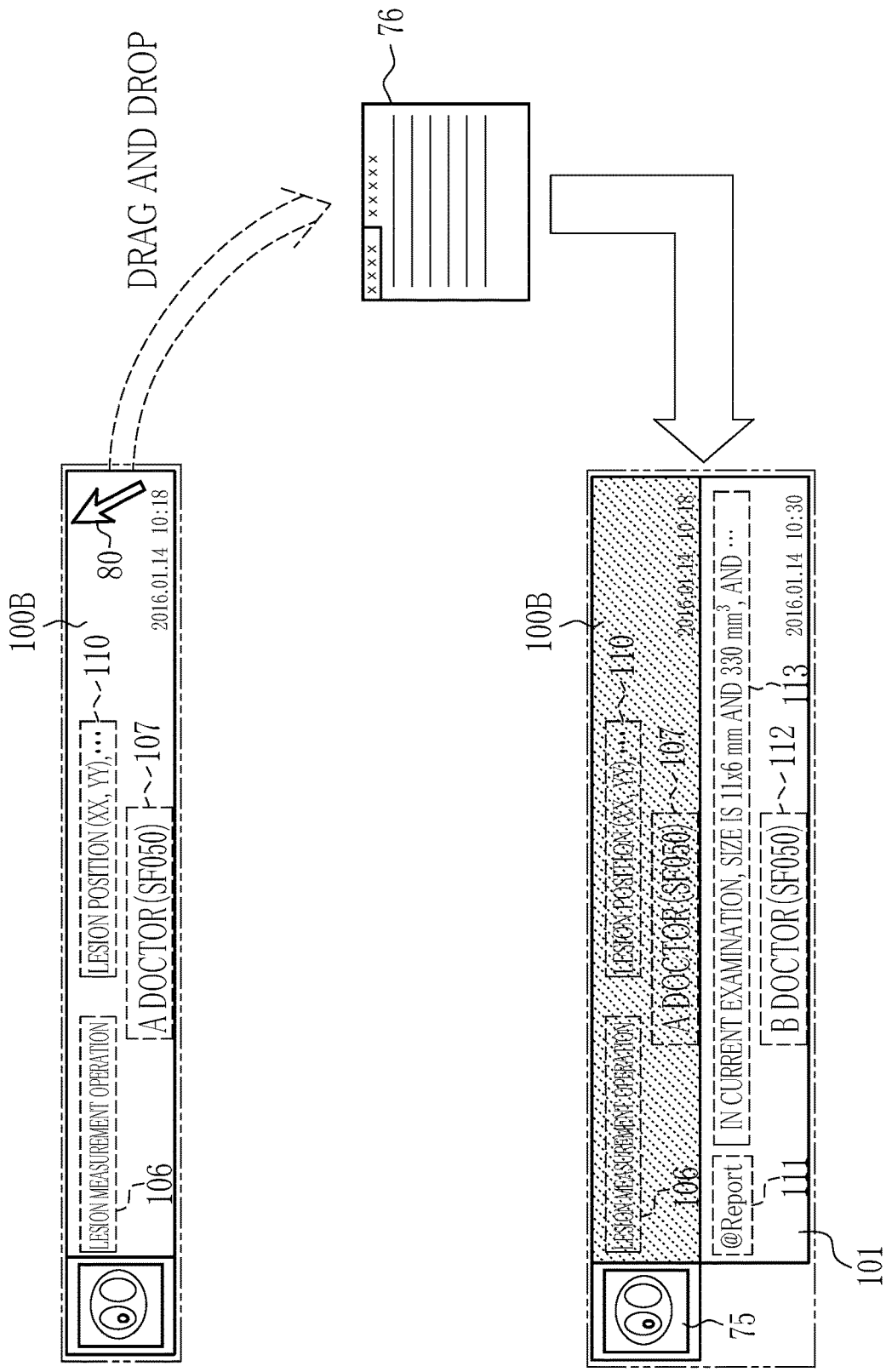
FIG. 22 is a diagram illustrating a second embodiment in which a display aspect of an automatic processing log or a manual operation log is varied depending on the number of times of quotation.

In the second embodiment illustrated in FIGS. 22 and 23, the display aspect of the automatic processing log APL or the manual operation log MOL is varied depending on the number of times of quotation.

FIG. 22 illustrates a method of quoting the diagnosis support information or the doctor's analysis result in the medical report 21 or the medical conference, as in FIG. 17. However, in FIG. 22, the display aspect of the automatic processing log APL or the manual operation log MOL is varied before and after the diagnosis support information or the doctor's analysis result is quoted, that is, between a case where the number of times of quotation is zero and a case where the number of times of quotation is one. More specifically, after the diagnosis support information or the doctor's analysis result is quoted, as indicated by hatching, the background color of the APL block 99 or the MOL block 100 (MOL block 100B in FIG. 22) is changed from the background color before the diagnosis support information or the doctor's analysis result is quoted.

FIG. 23 illustrates a change example of the background color of the APL block 99 or the MOL block 100 according to the number of times of quotation. That is, the background color of the APL block 99 or the MOL block 100 is white in a case where the number of times of quotation is zero, is yellow in a case where the number of times of quotation is one, is yellow-green in a case where the number of times of quotation is two, and is green in a case where the number of times of quotation is three or more. The screen output control unit 66 changes the background color of the APL block 99 or the MOL block 100 according to such a table, for example. In this manner, it is possible to immediately determine how many times the diagnosis support information or the doctor's analysis result is quoted.

The number of times of quotation can be known by counting the number of QL blocks 101. However, it takes time to count the number, and it is difficult to intuitively understand. Thus, by varying the display aspect of the automatic processing log APL or the manual operation log MOL depending on the number of times of quotation as described above, it is possible to more intuitively grasp the number of times of quotation.

It is considered that the automatic processing log APL or the manual operation log MOL of which the number of times of quotation of the diagnosis support information or the doctor's analysis result is large has higher doctor's attention degree and is more important than the one of which the number of times of quotation is small. Therefore, in a case where a display aspect in which the difference in the number of times of quotation can be quickly grasped is used, it is possible to quickly distinguish the important automatic processing log APL or manual operation log MOL and unimportant automatic processing log APL or manual operation log MOL.

As a method of varying the display aspect of the automatic processing log APL or the manual operation log MOL depending on the number of times of quotation, instead of or in addition to the method of changing the background color of the APL block 99 or the MOL block 100, a method of displaying a number indicating the number of times of quotation or a figure (for example, a circle) indicating the number of times of quotation by the number in the APL block 99 or the MOL block 100 may be adopted.

The display of the APL block 99 or the MOL block 100 may become less noticeable as the number of times of quotation is increased, for example, by graying out the APL block 99 or the MOL block 100 when the number of times of quotation becomes one.

Third Embodiment

Figure 24:
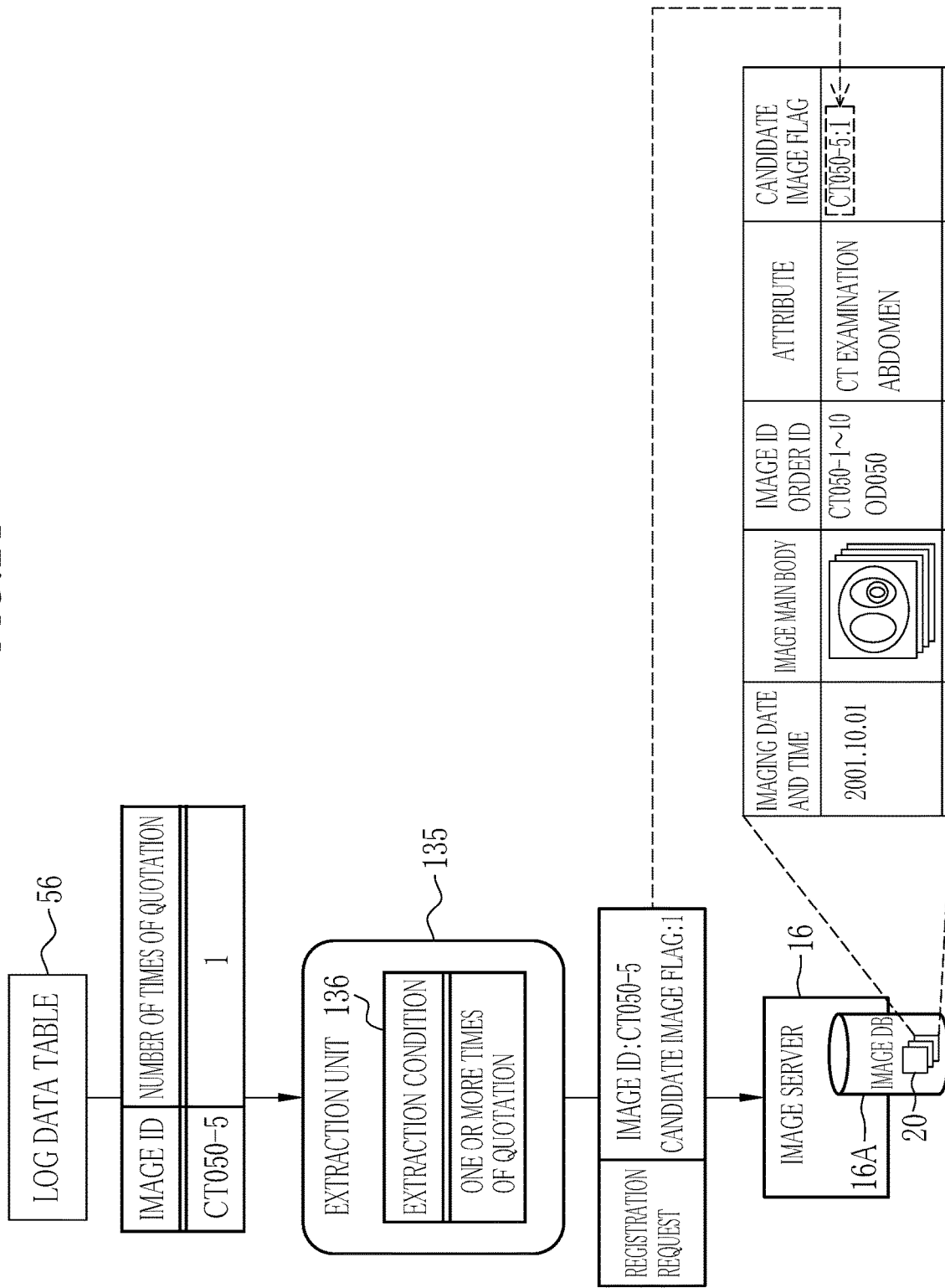
FIG. 24 is a diagram illustrating a third embodiment in which a medical image of which the number of times of quotation is equal to or greater than a threshold value is extracted as a candidate image for a similar case image similar to a medical image of a target patient, and illustrates a case in which the number of times of quotation is equal to or greater than a threshold value.
Figure 25:
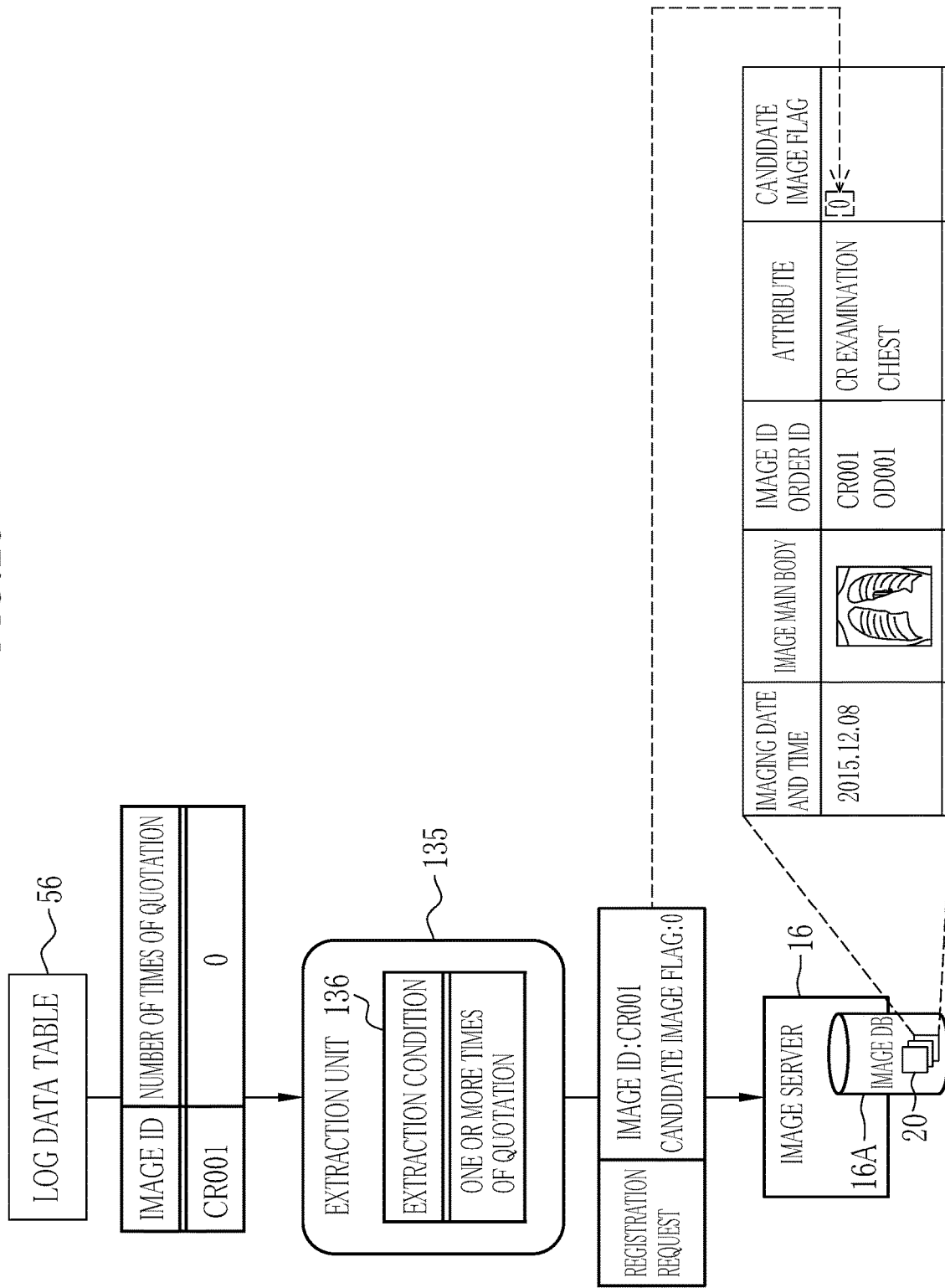
FIG. 25 is a diagram illustrating the third embodiment in which a medical image of which the number of times of quotation is equal to or greater than a threshold value is extracted as a candidate image for a similar case image similar to a medical image of a target patient, and illustrates a case in which the number of times of quotation is less than a threshold value.

In the third embodiment illustrated in FIGS. 24 and 25, a medical image 20 of which the number of times of quotation is equal to or greater than a threshold value is extracted as a candidate image for a similar case image similar to the medical image of the target patient.

In FIGS. 24 and 25, the CPU 42B of the medical examination support server 12 functions as an extraction unit 135 in addition to the processing units 60 to 66 in the first embodiment. The extraction unit 135 extracts a candidate image on the basis of the number of times of quotation.

More specifically, the extraction unit 135 reads the number of times of quotation of, for example, the doctor's analysis result (the number of times of quotation of the diagnosis support information, and a total of the number of times of quotation of the diagnosis support information and the number of times of quotation of the doctor's analysis result are also possible) for the medical image 20 having a certain image ID, from the log data table 56. Next, the extraction unit 135 collates the read number of times of quotation with an extraction condition 136 relating to the preset number of times of quotation. In FIGS. 24 and 25, the number of times of quotation of one or more is set in the extraction condition 136. The number of times of quotation of one corresponds to the threshold value.

In the embodiment, in a file of the medical images 20 for one case, an item of a candidate image flag is provided in addition to the items illustrated in FIG. 6 in the first embodiment. In the item of the candidate image flag, "1" is registered in a case where the corresponding medical image 20 is the candidate image, and "0" is registered in a case where the corresponding medical image 20 is not the candidate image.

The extraction unit 135 transmits a registration request for the candidate image flag according to the collation result to the image server 16. FIG. 24 illustrates a case in which the number of times of quotation for the medical image 20 read from the log data table 56 satisfies the extraction condition 136 (the number of times of quotation is equal to or greater than the threshold value). In this case, the extraction unit 135 transmits the registration request indicating that "1" is registered in the candidate image flag to the image server 16. In contrast, FIG. 25 illustrates a case in which the number of times of quotation for the medical image 20 read from the log data table 56 does not satisfy the extraction condition 136 (the number of times of quotation is less than the threshold value). In this case, the extraction unit 135 transmits the registration request indicating that "0" is registered in the candidate image flag to the image server 16.

At the time of searching for the similar case image, the medical image 20 for which "0" is registered in the candidate image flag is excluded from the candidate image. The similar case image is searched for from the medical images 20 for which "1" is registered in the candidate image flag.

In this manner, since the medical image 20 of which the number of times of quotation is equal to or greater than the threshold value becomes the candidate image for the similar case image, it is possible to search for the medical image 20, which is considered to have high doctor's attention degree and to be important, as the similar case image. In other words, it is possible to prevent the medical image 20, which is considered to be less important, from being searched for as the similar case image.

Fourth Embodiment

Figure 26:
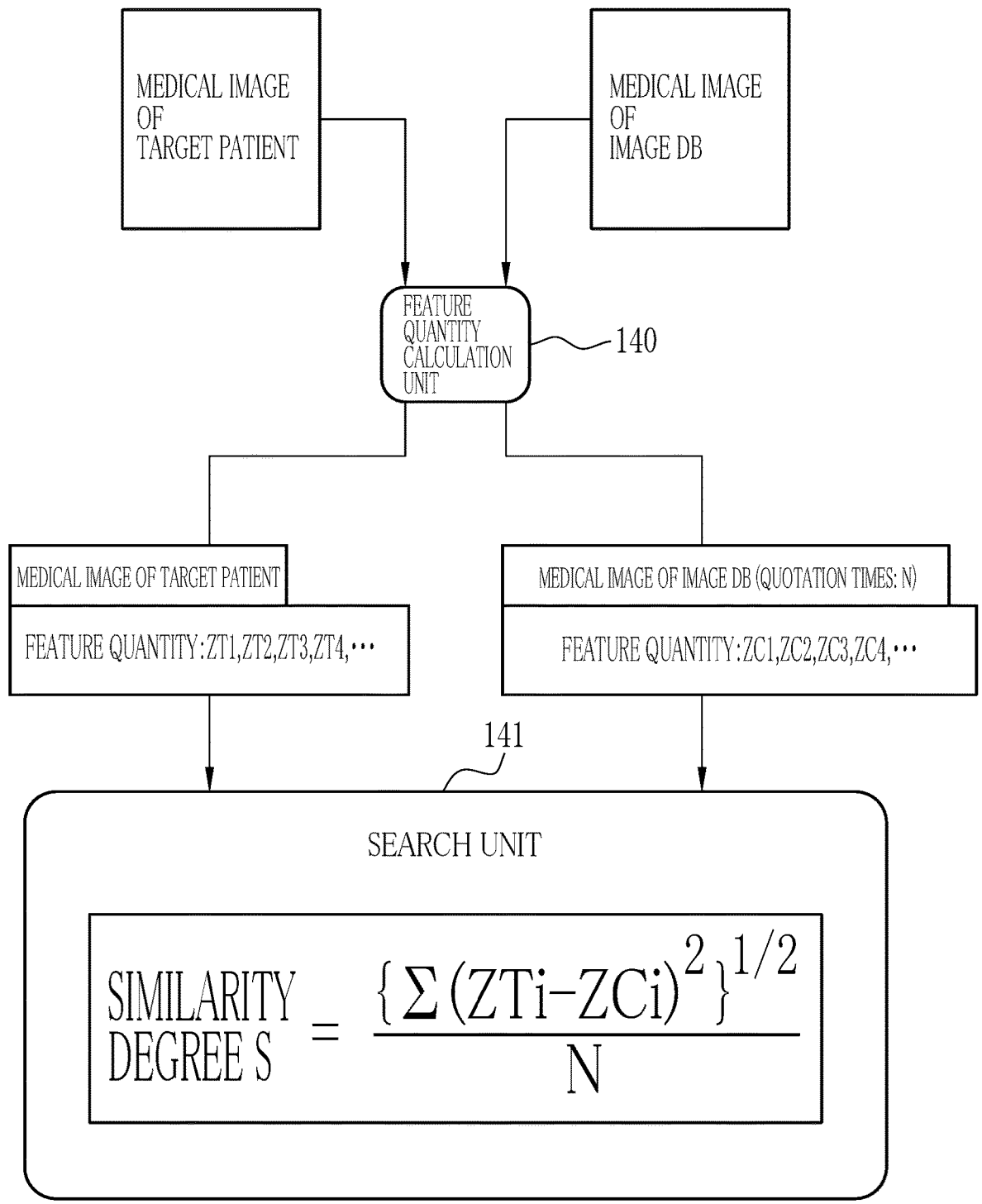
FIG. 26 is a diagram illustrating a fourth embodiment in which a similar case image similar to a medical image of a target patient is searched for using an equation with the number of times of quotation as a parameter.

In the fourth embodiment illustrated in FIG. 26, the similar case image similar to the medical image of the target patient is searched for by using an equation with the number of times of quotation as a parameter.

In FIG. 26, the CPU 42B of the medical examination support server 12 functions as a feature quantity calculation unit 140 and a search unit 141 in addition to the processing units 60 to 66 in the first embodiment. The feature quantity calculation unit 140 calculates a feature quantity Z of the medical image 20. The search unit 141 searches for the similar case image similar to the medical image 20 of the target patient from a plurality of medical images 20 of the image DB 16A.

The feature quantity Z includes the size of a lesion exemplified as the diagnosis support information in the first embodiment, a numerical value relating to a pixel value such as an average value or the standard deviation of pixel values of a lesion, a numerical value relating to the position of a lesion such as a distance to another lesion, a distance to the chest wall, and belonging lobes of the lungs such as an upper lobe, a middle lobe, a lower lobe, S1, and S2. In addition to the above description, the feature quantity Z also includes a degree of irregularity of the lesion margin, a concentration gradient at the boundary between a lesion and a normal portion, a spiculation degree such as the number and length of the spiculation, and a cavity size. In this manner, there are a plurality of types of the feature quantity Z.

The feature quantity calculation unit 140 calculates a feature quantity ZTi (i=1, 2, 3, 4, . . . ) of the medical image 20 of the target patient, and a feature quantity ZCi of the medical image 20 of the image DB 16A. The feature quantity calculation unit 140 outputs the calculated feature quantities ZTi and ZCi to the search unit 141. A multidimensional vector with a plurality of types of feature quantity Z such as feature quantities ZTi and ZCi as elements is called a feature vector.

The search unit 141 calculates a similarity degree S between the medical image 20 of the target patient and the medical image 20 of the image DB 16A using Equation (1) described below.

$$S=[\{\Sigma(ZTi-ZCi)^2\}^{1/2}]/N \qquad (1)$$

Here, N is the number of times of quotation of, for example, the doctor's analysis result (the number of times of quotation of the diagnosis support information, and a total of the number of times of quotation of the diagnosis support information and the number of times of quotation of the doctor's analysis result are also possible) relating to the medical image 20 of the image DB 16A. That is, Equation (1) is an equation with the number of times of quotation as a parameter.

In Equation (1), the right side numerator is a square root of the sum of squares of the difference (ZTi−ZCi) between a plurality of types of feature quantity ZTi of the medical image 20 of the target patient and a plurality of types of feature quantity ZCi of the medical image 20 of the image DB 16A, that is, the distance between a feature vector having the feature quantity ZTi as an element and a feature vector having the feature quantity ZCi as an element. Therefore, since the distance between a feature vector having the feature quantity ZTi as an element and a feature vector having the feature quantity ZCi as an element becomes short as the similarity between the medical image 20 of the target patient and the medical image 20 of the image DB 16A is increased, the value of the right side numerator in Equation (1) becomes smaller. Since the similarity degree S is obtained by dividing the distance between the feature vectors by the number of times of quotation N, the similarity degree S is decreased as the number of times of quotation N is increased.

The search unit 141 searches for the medical image 20 of the image DB 16A having a similarity degree S equal to or less than a threshold value, as the similar case image. In a case where there are a plurality of medical images 20 of the image DB 16A with almost the same value of the right side numerator in Equation (1), the medical image 20 of which the number of times of quotation N is higher has a smaller similarity degree S (higher similarity), and thus is more easily searched for as the similar case image.

In this manner, since the similar case image is searched for by using an equation with the number of times of quotation as a parameter, it is possible to search for the medical image 20, which is considered to have high doctor's attention degree and to be important, as the similar case image.

As the feature quantity, instead of the feature quantity calculated by the feature quantity calculation unit 140, the doctor's analysis result may be used. In this case, whether to use the feature quantity calculated by the feature quantity calculation unit 140 or to use the doctor's analysis result may be selected depending on the number of times of quotation, such as a case in which the doctor's analysis result is used as the feature quantity in a case where the number of times of quotation of the doctor's analysis result is greater than the number of times of quotation of the diagnosis support information for a certain medical image 20.

Fifth Embodiment

Figure 27:
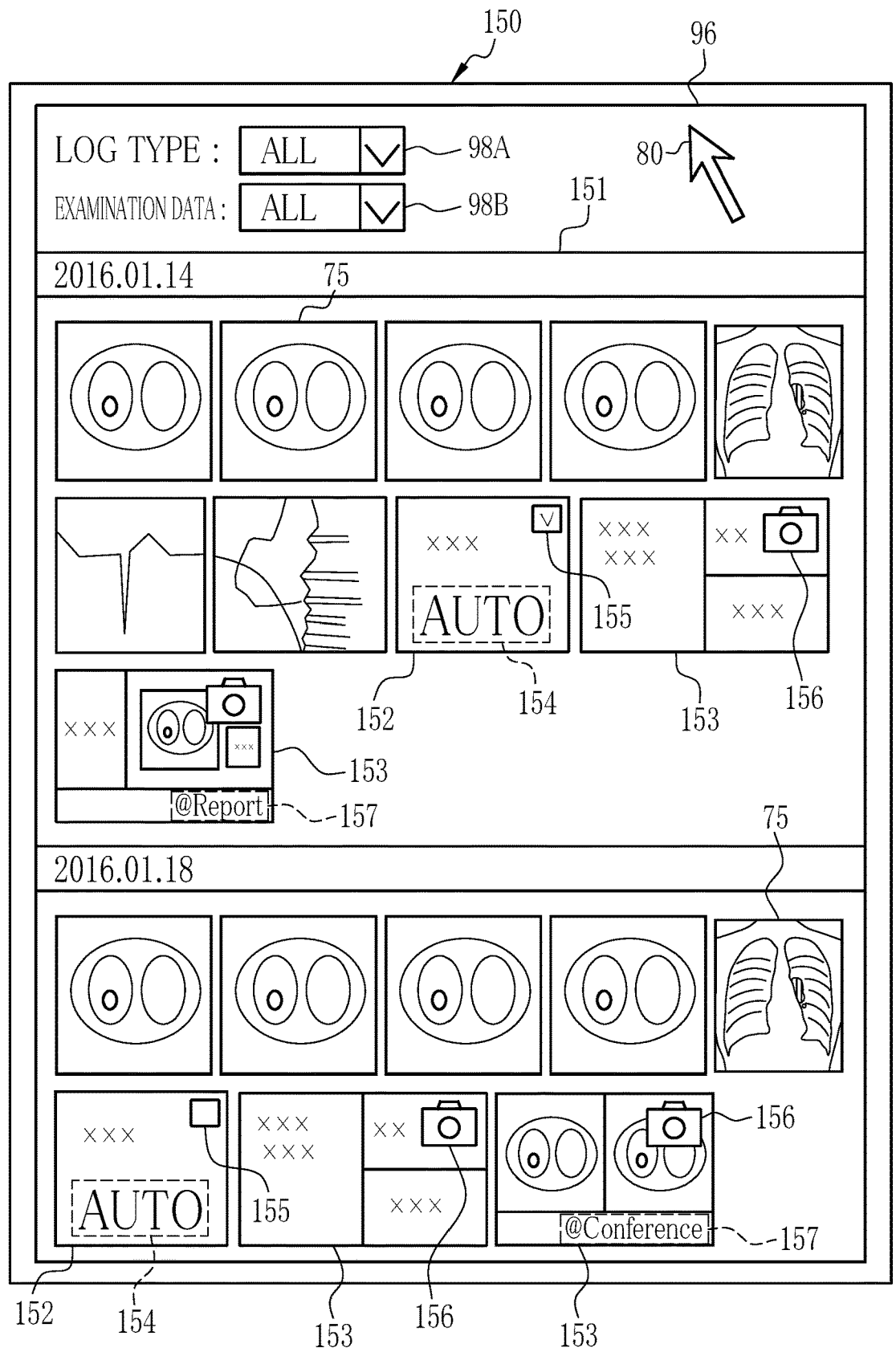
FIG. 27 is a diagram illustrating another example of a log display screen.
Figure 28:
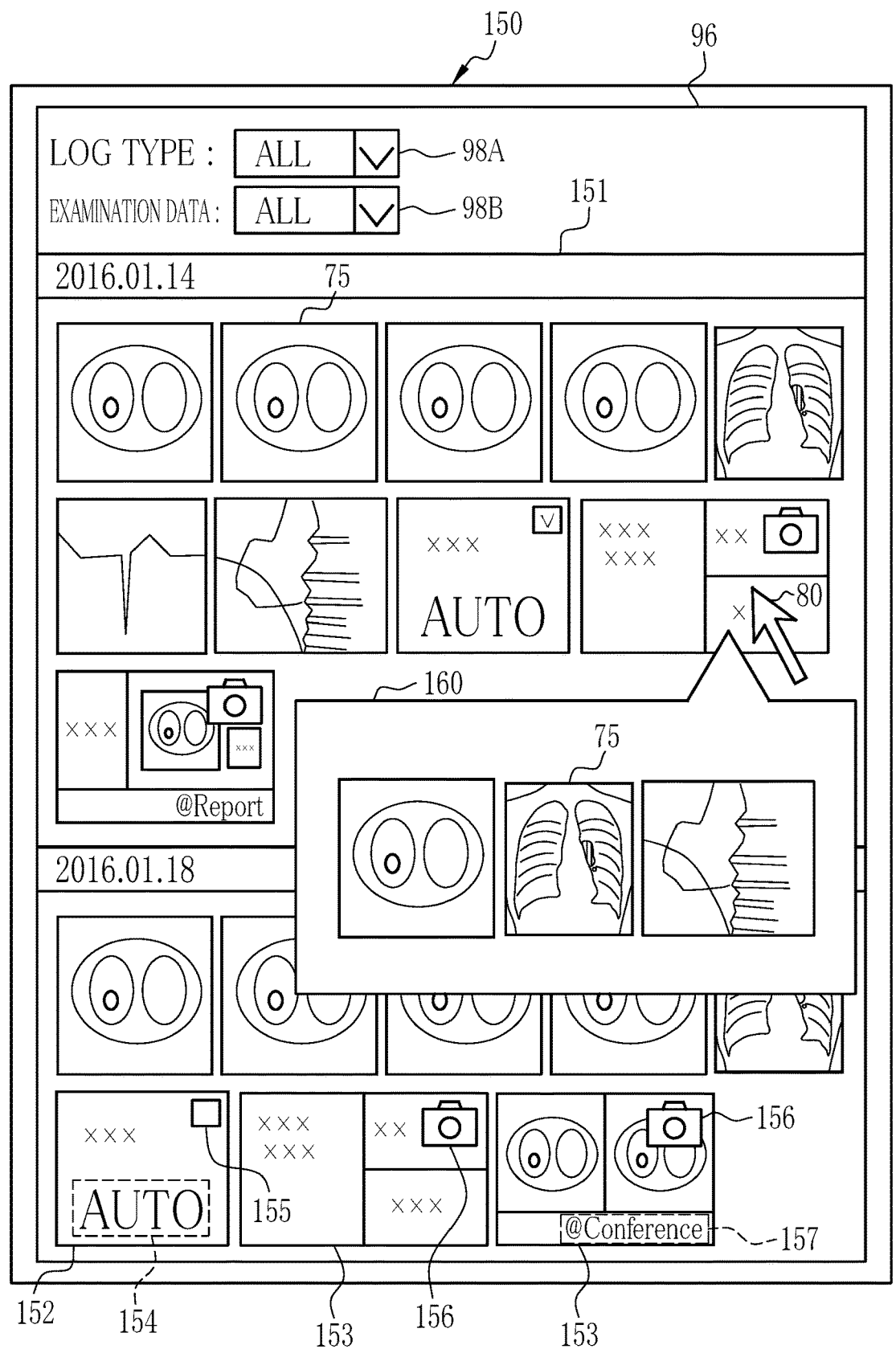
FIG. 28 is a diagram illustrating a log display screen that displays a balloon in which examination data associated with a display block of a manual operation log where the cursor is placed is collectively displayed.
Figure 29:
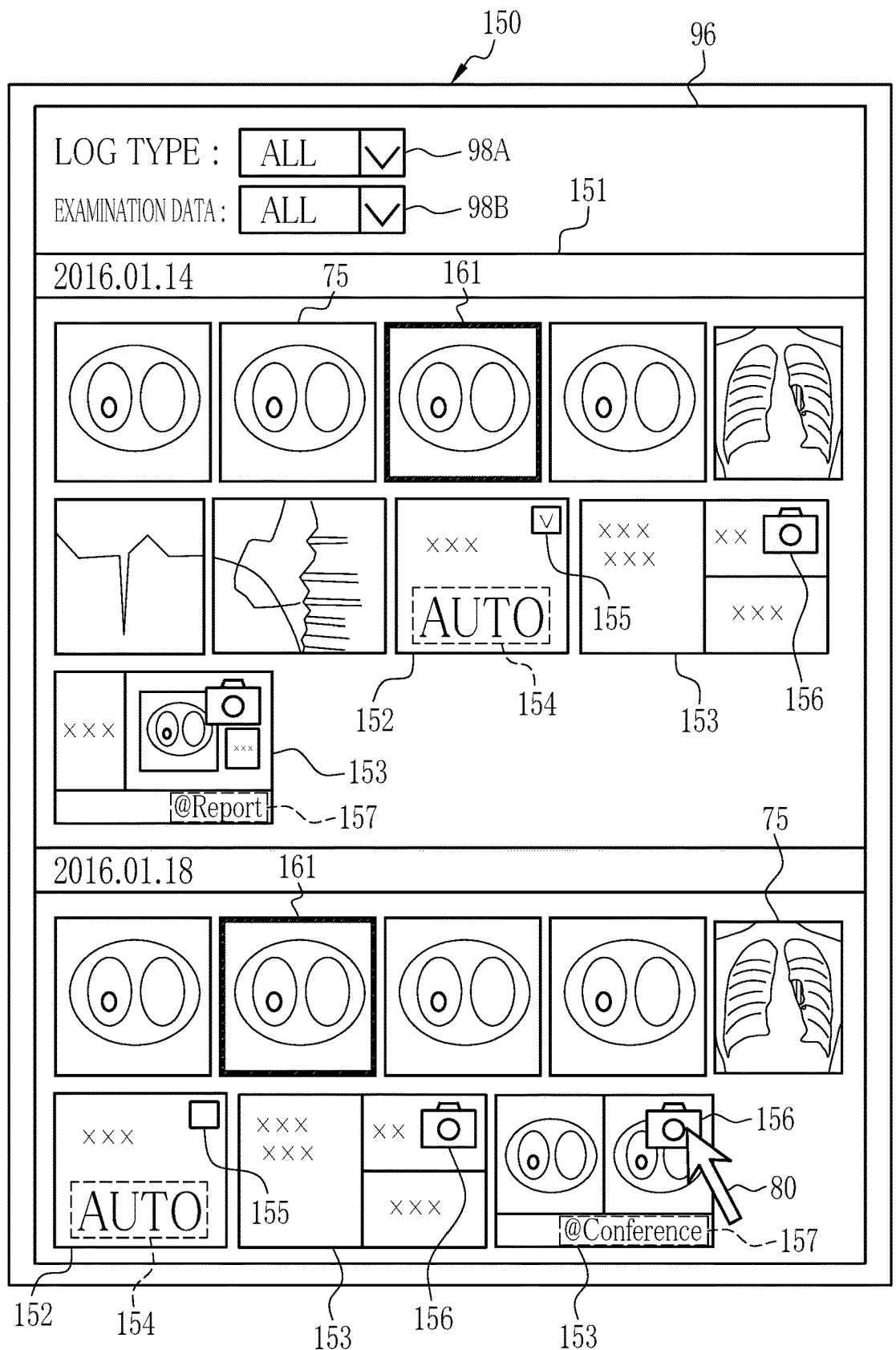
FIG. 29 is a diagram illustrating a log display screen that displays a frame in examination data associated with a display block of a manual operation log where the cursor is placed.

The fifth embodiment illustrated in FIGS. 27 to 29 is modification examples of the log display screen.

In FIG. 27, a log display screen 150 of the embodiment has a partial function of the integrated display screen 35 in a collective display region 151. That is, in the collective display region 151, the thumbnail 75 of the medical image 20 is displayed. The thumbnail 75 in the collective display region 151 can also be selected by the cursor 80, and in a case where the thumbnail 75 is selected by the cursor 80, the viewer screen 85 is displayed.

The collective display region 151 is divided into small regions for each day. In each small region, the thumbnails 75 of the medical images 20 acquired in the image examination performed on the day are displayed by being arranged from left to right and from top to bottom in order of imaging date and time.

In each small region of the collective display region 151, APL blocks 152 and MOL blocks 153 which have the same size as the thumbnail 75 are displayed by being arranged from left to right and from top to bottom in order of registration date and time, similar to the thumbnail 75. As in the APL block 99 in the first embodiment, in the APL block 152, a character notation (AUTO) 154 indicating deriving from the automatic processing of the diagnosis support algorithm 30 is written. Further, in the APL block 152, a character notation (not illustrated) indicating a part of the diagnosis support information with a small size is written.

Further, in the APL block 152, a checkbox 155 is provided instead of the character notation 109, which indicates whether the detailed information has been displayed or has not been displayed, of the APL block 99 in the first embodiment. In a case where the detailed information has been displayed, a check mark is displayed in the checkbox 155.

The MOL block 153 includes display state information, that is, a thumbnail of a screenshot of the display 23 at the time of acquisition of the manual operation log MOL. In the MOL block 153, a camera mark 156 indicating being a screenshot is displayed. The MOL block 153 is distinguishable from the APL block 152 by the camera mark 156.

As indicated by a frame with a broken line and reference numeral 157, a character notation is written in the APL block 152 of the automatic processing log APL of which the diagnosis support information is quoted in the medical report 21 or the medical conference, or in the MOL block 153 of the manual operation log MOL of which the doctor's analysis result is quoted in the medical report 21 or the medical conference. FIG. 27 illustrates an example in which characters (@Conference) indicating that the doctor's analysis result is quoted in the medical conference are written.

In the log display screen 150, the display indicating that the diagnosis support information or the doctor's analysis result is quoted in the medical report 21 or the medical conference is completed by the character notation 157. That is, the QL block 101 in the first embodiment is not displayed. In this manner, the QL block 101 may not be necessarily displayed in the invention.

As illustrated in FIG. 28, in the log display screen 150, in a case where a state where the cursor 80 is placed on the MOL block 153 is continued for a predetermined time (for example, 3 seconds), a balloon 160 is displayed near the MOL block 153. In the balloon 160, the examination data associated with the manual operation log MOL of the MOL block 153 where the cursor 80 is placed is collectively displayed. FIG. 28 illustrates a state in which the manual operation log MOL of the MOL block 153 where the cursor 80 is placed relates to the enlarged display operation of the CT image, the CR image, and the CAG image, and the thumbnail 75 of each image thereof is displayed in the balloon 160.

In the log display screen 150, the MOL block 153 has the same size as the thumbnail 75. Therefore, it is not clear what kind of examination data the manual operation log MOL is associated with, only by the display of the MOL block 153. Thus, the examination data associated with the manual operation log MOL of the MOL block 153 is specified in the balloon 160. In this manner, the examination data associated with the manual operation log MOL of the MOL block 153 can be easily confirmed.

FIG. 29 illustrates another method of specifying the examination data associated with the manual operation log MOL of the MOL block 153. In this case, in a case where a state where the cursor 80 is placed on the MOL block 153 is continued for a predetermined time (for example, 3 seconds) as in FIG. 28, a frame 161 is displayed in the examination data associated with the manual operation log MOL of the MOL block 153 where the cursor 80 is placed. FIG. 29 illustrates a state in which the manual operation log MOL of the MOL block 153 where the cursor 80 is placed relates to the comparison display operation between the CT image captured on "2016.01.14" and the CT image captured on "2016.01.18", and the frame 161 is displayed on the thumbnail 75 of each image thereof. The examination data associated with the manual operation log MOL of the MOL block 153 can be easily confirmed even by the display of the frame 161.

Both the balloon 160 and the frame 161 may be displayed. Further, instead of or in addition to the balloon 160 or the frame 161, the reproduction screen 130 illustrated in FIG. 19B may be displayed.

The character notations 111 and 157 indicating that the diagnosis support information or the doctor's analysis result is quoted in the medical report 21 or the medical conference may have a function of a hyperlink to the medical report 21 or the conference information 22. In this manner, it is possible to quickly refer to the medical report 21 or the conference information 22.

In the medical report 21 or the medical conference, a medical image 20 other than that of the target patient is also quoted. Such a medical image 20 is often useful as information for grasping the medical state of the target patient, such as a similar case image. Therefore, in a case where it is possible to quickly refer to the medical report 21 or the conference information 22, it is possible to quickly grasp the medical state of the target patient, which is efficient.

In each embodiment described above, as the examination data of which the APL blocks 99 and 152 and the MOL blocks 100 and 153 are displayed, the medical image 20 is exemplified, but the invention is not limited thereto. The APL blocks 99 and 152 and the MOL blocks 100 and 153 of the measurement data such as vital signs, blood tests, urine tests may be displayed.

The log display screens 95 and 150 may not always be displayed together with the integrated display screen 35. When a new log is added to the log data table 56, the log display screens 95 and 150 may be displayed in a pop-up on the integrated display screen 35.

An item of a disease may be provided to the log data table 56, and the disease may be associated with each log. In this manner, in case of a target patient with a plurality of diseases, it is possible to narrow down logs using the disease.

The hardware configuration of a computer which constitutes the medical examination support server 12 corresponding to the medical examination support apparatus of the invention can be modified in various ways. For example, in order to improve the processing capacity and reliability, the medical examination support server 12 may be constituted by a plurality of server computers that are separated from each other as hardware. For example, the functions of the request receiving unit 60 and the second acquisition unit 64, the functions of the medical data acquisition unit 61, the analysis processing unit 62, and the first acquisition unit 63, and the functions of the information management unit 65 and the screen output control unit 66 are distributed to three server computers. In this case, the three server computers constitute the medical examination support apparatus.

In each embodiment described above, an aspect in which the medical examination support server 12 generates various display screens and the various display screens are reproduced by the client terminal 11 and displayed on the display 23 on the basis of the screen data of the various display screens from the medical examination support server 12 is exemplified. However, data which is a source for generating various display screens may be transmitted from the medical examination support server 12 to the client terminal 11 and the client terminal 11 may generate the various display screens. In this case, the screen output control unit 66 is constructed in the CPU 42A of the client terminal 11.

Further, each processing unit constructed in the CPU 42B of the medical examination support server 12 may be constructed in the CPU 42A of the client terminal 11, and the client terminal 11 may be operated as the medical examination support apparatus. In this case, the request receiving unit 60 directly receives instructions from the GUI control unit 50 instead of the distribution request or the like. In addition, the screen output control unit 66 outputs the generated various display screens to the GUI control unit 50. Further, the electronic medical record server 15 or the image server 16 may be operated as the medical examination support apparatus.

In this manner, the hardware configuration of a computer can be appropriately changed according to the required performance, such as processing capacity, safety, or reliability. Further, in order to ensure the safety and the reliability, without being limited to hardware, an application program such as the operation program 55 may be duplicated or may be distributed and stored in a plurality of storage devices.

In each embodiment described above, an aspect in which the medical examination support server 12 is used in one medical facility is described, but an aspect in which the medical examination support server 12 is used by a plurality of medical facilities may be adopted.

In each embodiment described above, the medical examination support server 12 is communicably connected to the client terminal 11, which is installed in one medical facility, through the network 13 such as a LAN, and provides various display screens in response to the distribution request from the client terminal 11. In order for the medical examination support server 12 to be used by a plurality of medical facilities, the medical examination support server 12 is communicably connected to each of the client terminals 11 installed in the plurality of medical facilities, for example, through a wide area network (WAN) such as the Internet or a public communication network. Then, the medical examination support server 12 receives the distribution request from each client terminal 11 of the plurality of medical facilities through the WAN, and provides various display screens to each client terminal 11. In case of using the WAN, it is preferable to construct a virtual private network (VPN) or to use a communication protocol with a high security level, such as hypertext transfer protocol secure (HTTPS), in consideration of information security.

In this case, the electronic medical record 19, the medical image 20, the medical report 21, the conference information 22, and the log data table 56 are managed for each medical facility. Further, the installation location and operating entity of the medical examination support server 12 in this case may be a data center operated by a company that is different from the medical facilities, or may be one of the plurality of medical facilities, for example.

It is sufficient that the medical examination support apparatus of the invention has at least the function of controlling the output of the log display screen 95, and thus the medical examination support apparatus of the invention may not necessarily have the function of controlling the output of the integrated display screen 35 as in the screen output control unit 66 in each embodiment described above.

In each embodiment described above, the hardware structure of the processing units executing various kinds of processing, such as the request receiving unit 60, the medical data acquisition unit 61, the analysis processing unit 62, the first acquisition unit 63, the second acquisition unit 64, the information management unit 65, the screen output control unit 66, the extraction unit 135, the feature quantity calculation unit 140, and the search unit 141 is various processors as follows.

The various processors include a CPU, a programmable logic device (PLD), dedicated electrical circuitry, and the like. The CPU is a general-purpose processor functioning as various processing units by executing software (program) as being well known. The PLD is a processor of which the circuit configuration can be changed after manufacture, such as a field programmable gate array (FPGA). The dedicated electrical circuitry is a processor having a circuit configuration designed exclusively to execute specific processing, such as an application specific integrated circuit (ASIC).

One processing unit may be configured by one of the various processors or a combination of the same or different kinds of two or more processors (for example, a combination of a plurality of FPGAs or a combination of a CPU and an FPGA). In addition, a plurality of processing units may be configured by one processor. As an example where a plurality of processing units are configured by one processor, first, there is an aspect where one processor is configured by a combination of one or more CPUs and software, and this processor functions as a plurality of processing units. Second, there is an aspect where a processor fulfilling the functions of the entire system including a plurality of processing units by one IC chip as typified by a system on chip (SoC) or the like is used. In this manner, various processing units are configured by using one or more of the above-described various processors as hardware structures.

Furthermore, the hardware structures of these various processors are more specifically electrical circuitry where circuit elements, such as semiconductor elements, are combined.

From the above description, the medical examination support apparatus described in Additional remark 1 described below can be grasped.

[Additional remark 1] A medical examination support apparatus comprising:

a first acquisition processor that acquires an automatic processing log which is a history of automatically performing analysis processing on examination data obtained in a medical examination performed on a patient by a diagnosis support algorithm to output a result of the analysis processing as diagnosis support information for supporting diagnosis of a doctor;

a second acquisition processor that acquires a manual operation log which is a history of a manual operation of the doctor with respect to the examination data;

an information management processor that stores the examination data in association with the automatic processing log and the manual operation log in a storage unit; and a screen output control processor that controls an output of a log display screen which has a collective display region in which the automatic processing log and the manual operation log are collectively displayed in a time series in a distinguishable manner.

In the invention, it is also possible to appropriately combine the above-described various embodiments or various modification examples. Further, without being limited to the embodiments described above, various configurations can be adopted as long as the configurations do not depart from the scope of the invention. In addition to the program, the invention also extends to a storage medium that stores the program.

EXPLANATION OF REFERENCES

10: medical examination system
11: client terminal
12: medical examination support server (medical examination support apparatus)
13: network
14: server group
15: electronic medical record server
15A: medical record database (DB)
16: image server
16A: image database (DB)
17: report server
17A: report database (DB)
18: conference server
18A: conference database (DB)
19: electronic medical record
20: medical image
21: medical report
22: conference information
23, 44: display
24, 45: input device
30: diagnosis support algorithm
35: integrated display screen
40, 40B: storage device (storage unit)
41: memory
42, 42A, 42B: CPU
43: communication unit
46: data bus
50: GUI control unit
51: browser control unit
55: operation program
56: log data table
60: request receiving unit
61: medical data acquisition unit
62: analysis processing unit
63: first acquisition unit
64: second acquisition unit 65: information management unit
66: screen output control unit
70: first display region
71: second display region
72: third display region
73: fourth display region
75: thumbnail
76: report window
77: conference window
80: cursor
85: viewer screen
86, 122: image display region
87: information display region
88: measurement result input region
89: frame
90: registration button
95, 150: log display screen
96: display selection region
97, 151: collective display region
98A, 98B: pull-down menu
99, 152: display block of automatic processing log (APL block)
100, 100A, 100B, 153: display block of manual operation log (MOL block)
101: display block of quotation log (QL block)
105 to 113, 154, 157: character notation
120: detailed information display screen
121: algorithm display region
123: diagnosis support information display region
130: reproduction screen
135: extraction unit
136: extraction condition
140: feature quantity calculation unit
141: search unit
155: checkbox
156: camera mark
160: balloon
161: frame
APL: automatic processing log
MOL: manual operation log
QL: quotation log
ST100 to ST180, ST200, ST210: step
Z, ZTi, ZCi: feature quantity
S: similarity degree
N: number of times of quotation

What is claimed is:

1. A medical examination system comprising:
a medical examination support apparatus;
an electronic medical record server with a medical record database;
an image server with an image database;
a report server with a report database;
a conference server with a conference database; and
a processor configured to:
  in response to a distribution request for an integrated display screen in which various kinds of medical data are combined into one from a client terminal communicatively coupled to the medical examination support apparatus, acquire a medical data from the electronic medical record server, the image server, the report server and the conference server by performing a search on the medical record database, the image database and the report database;
  in response to the distribution request, acquire an automatic processing log which is a history of automatically performing analysis processing on examination data obtained in a medical examination by a diagnosis support algorithm to output a result of the analysis processing as diagnosis support information configured for supporting diagnosis;
  in response to a registration request for an operation log from the client terminal, acquire the operation log which is a history of an operation with respect to the examination data comprising an enlarged display operation or a comparison display operation;
  store the examination data in association with the automatic processing log and the operation log in a storage; and
  control an output of a log display screen which has a collective display region in which the automatic processing log and the operation log are collectively displayed in a time series in a distinguishable manner,
wherein the operation log includes an analysis result for the examination data,
wherein the processor causes a quotation log to be displayed in the collective display region to correspond to the automatic processing log or the operation log, the quotation log being a history of quoting the diagnosis support information included in the automatic processing log or the analysis result included in the operation log via a drag-and-drop operation in a medical report stored in the report database or a medical conference information stored in the conference database,
wherein the processor stores the number of times of quotation of the diagnosis support information included in the automatic processing log or the analysis result included in the operation log, in the medical report or the medical conference information in association with the automatic processing log or the operation log in the storage,
wherein the processor varies a display aspect of the automatic processing log or the operation log depending on the number of times of quotation read out from the storage,
wherein the processor generates the integrated display screen and the log display screen, and transmits the integrated display screen and the log display screen to the client terminal, in response to the distribution request for the integrated display screen from the client terminal,
wherein the processor is further configured to searches for a similar case image similar to a target medical image using an equation $S=[\{\Sigma(ZTi-ZCi)^2\}^{1/2}/N$ from the image database, wherein S is a similarity degree between the target medical image and a medical image of the image database, ZTi is a feature quantity of the target medical image, ZCi is a feature quantity of the medical image of the image database, N is a number of times of quotation, i is a natural number, the feature quantity includes a size of a lesion, a numerical value relating to a pixel value and a numerical value relating to the position of a lesion, wherein the medical image of the image database having the similarity degree equal to or less than a threshold value is searched as the similar case image.

2. The medical examination support apparatus according to claim 1,
wherein the medical examination is an image examination,
the examination data is a medical image, and
the processor is further configured to function as an extraction unit that extracts the medical image of which the number of times of quotation is equal to or greater than a quotation number threshold value, as a candidate image for a similar case image similar to a medical image.

3. The medical examination support apparatus according to claim 1,
wherein a selection instruction of the automatic processing log is received in the collective display region, and
the screen output control unit displays detailed information, which includes the diagnosis support information, of the automatic processing log of which the selection instruction has been received, and varies a display aspect between the automatic processing log of which the selection instruction has been received and the detailed information has been displayed, and the automatic processing log of which the selection instruction has not been received and the detailed information has not been displayed.

4. The medical examination support apparatus according to claim 1,
wherein a selection instruction of the operation log is received in the collective display region,
the information management unit stores display state information representing a display state of the examination data at a time of acquisition of the operation log, in association with the operation log in the storage, and
the screen output control unit reproduces the display state of the examination data of the operation log of which the selection instruction has been received, on the basis of the display state information.

5. An operation method of a medical examination system comprising a medical examination support apparatus, an electronic medical record server with a medical record database, an image server with an image database, a report server with a report database and a conference server with a conference database, the operation method comprising:
a step of acquiring a medical data from the electronic medical record server, the image server, the report server and the conference server by performing a search on the medical record database, the image database and the report database in response to a distribution request for an integrated display screen in which various kinds of medical data are combined into one from a client terminal communicatively coupled to the medical examination support apparatus;
a step of acquiring an automatic processing log in response to the distribution request, wherein the automatic processing log is a history of automatically performing analysis processing on examination data obtained in a medical examination by a diagnosis support algorithm to output a result of the analysis processing as diagnosis support information configured for supporting diagnosis;
a step of acquiring an operation log which is a history of an operation with respect to the examination data in response to a registration request for the operation log from the client terminal;
a step of storing the examination data in association with the automatic processing log and the operation log in a storage;
a step of controlling an output of a log display screen which has a collective display region in which the automatic processing log and the operation log are collectively displayed in a time series in a distinguishable manner, and
a step of searching for a similar case image similar to a target medical image using an equation $S=[\}\Sigma(ZTi-ZCi)^2\}^{1/2}]/N$ from the image database, wherein S is a similarity degree between the target medical image and a medical image of the image database, ZTi is a feature quantity of the target medical image, ZCi is a feature quantity of the medical image of the image database, N is a number of times of quotation, i is a natural number, the feature quantity includes a size of a lesion, a numerical value relating to a pixel value and a numerical value relating to the position of a lesion, wherein the medical image of the image database having the similarity degree equal to or less than a threshold value is searched as the similar case image,
wherein the operation log includes an analysis result for the examination data,
wherein in the step of controlling the output of the log display screen, a quotation log is caused to be displayed in the collective display region to correspond to the automatic processing log or the operation log, the quotation log being a history of quoting the diagnosis support information included in the automatic processing log or the analysis result included in the operation log via a drag-and-drop operation in a medical report stored in the report database or a medical conference information stored in the conference database,
wherein in the step of storing the examination data, the number of times of quotation of the diagnosis support information included in the automatic processing log or the analysis result included in the operation log, in the medical report or the medical conference information is stored in association with the automatic processing log or the operation log in the storage,
wherein in the step of controlling the output of the log display screen, a display aspect of the automatic processing log or the operation log varies depending on the number of times of quotation read out from the storage,
wherein in the step of controlling the output of the log display screen, the integrated display screen and the log display screen are generated and transmitted to the client terminal in response to the distribution request for the integrated display screen from the client terminal.

6. A non-transitory computer readable medium for storing a computer-executable program for a medical examination system comprising a medical examination support apparatus, an electronic medical record server with a medical record database, an image server with an image database, a report server with a report database and a conference server with a conference database, the computer-executable program causing a computer to execute:
a function of acquiring a medical data from the electronic medical record server, the image server, the report server and the conference server by performing a search on the medical record database, the image database and the report database in response to a distribution request for an integrated display screen in which various kinds of medical data are combined into one from a client terminal communicatively coupled to the medical examination support apparatus;
a function of acquiring an automatic processing log in response to the distribution request, wherein the automatic processing log is a history of automatically performing analysis processing on examination data obtained in a medical examination by a diagnosis support algorithm to output a result of the analysis processing as diagnosis support information configured for supporting diagnosis;

a function of acquiring an operation log which is a history of an operation with respect to the examination data in response to a registration request for the operation log from the client terminal;

a function of storing the examination data in association with the automatic processing log and the operation log in a storage;

a function of controlling an output of a log display screen which has a collective display region in which the automatic processing log and the operation log are collectively displayed in a time series in a distinguishable manner, and a function of searching for a similar case image similar to a target medical image using an equation $S=[\{\Sigma(ZTi-ZCi)^2\}^{1/2}]/N$ from the image database, wherein S is a similarity degree between the target medical image and a medical image of the image database, ZTi is a feature quantity of the target medical image, ZCi is a feature quantity of the medical image of the image database, N is a number of times of quotation, i is a natural number, the feature quantity includes a size of a lesion, a numerical value relating to a pixel value and a numerical value relating to the position of a lesion, wherein the medical image of the image database having the similarity degree equal to or less than a threshold value is searched as the similar case image, wherein the operation log includes an analysis result for the examination data, wherein the function of controlling the output of the log display screen causes a quotation log to be displayed in the collective display region to correspond to the automatic processing log or the operation log, the quotation log being a history of quoting the diagnosis support information included in the automatic processing log or the analysis result included in the operation log via a drag-and-drop operation in a medical report stored in the report database or a medical conference information stored in the conference database, wherein the function of storing the examination data stores the number of times of quotation of the diagnosis support information included in the automatic processing log or the analysis result included in the operation log, in the medical report or the medical conference information in association with the automatic processing log or the operation log in the storage, wherein the function of controlling the output of the log display screen varies a display aspect of the automatic processing log or the operation log depending on the number of times of quotation read out from the storage, wherein the function of controlling the output of the log display screen generates the integrated display screen and the log display screen, and transmits the integrated display screen and the log display screen to the client terminal, in response to the distribution request for the integrated display screen from the client terminal.

* * * * *